(12) United States Patent
Davis et al.

(10) Patent No.: US 8,679,827 B2
(45) Date of Patent: Mar. 25, 2014

(54) APPARATUS AND METHODS FOR ANALYTE MEASUREMENT AND IMMUNOASSAY

(75) Inventors: Graham Davis, Princeton, NJ (US); Imants Lauks, Ottawa (CA); Chao Lin, San Diego, CA (US); Cary James Miller, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 121 days.

(21) Appl. No.: 13/495,224

(22) Filed: Jun. 13, 2012

(65) Prior Publication Data

US 2012/0305409 A1 Dec. 6, 2012

Related U.S. Application Data

(62) Division of application No. 13/198,253, filed on Aug. 4, 2011, now Pat. No. 8,222,024, which is a division of application No. 12/165,925, filed on Jul. 1, 2008, now Pat. No. 8,017,382, which is a division of application No. 10/087,730, filed on Mar. 5, 2002, now Pat. No. 7,419,821.

(51) Int. Cl.
*C12M 3/00* (2006.01)

(52) U.S. Cl.
USPC ......... 435/288.5; 435/7.1; 435/7.9; 435/7.94; 435/283.1; 435/285.2; 435/287.2; 435/287.1

(58) Field of Classification Search
USPC ................ 435/7.1, 7.9, 285.2, 287.1, 287.2, 435/288.5; 436/518; 422/50, 81, 82.01
See application file for complete search history.

(56) References Cited

U.S. PATENT DOCUMENTS

| | | |
|---|---|---|
| 4,018,886 A | 4/1977 | Giaever |
| 4,233,144 A | 11/1980 | Pace et al. |
| 4,238,757 A | 12/1980 | Schenck |
| 4,334,880 A | 6/1982 | Malmros |
| 4,781,683 A | 11/1988 | Wozniak et al. |
| 4,830,959 A | 5/1989 | McNeil et al. |
| 4,916,075 A | 4/1990 | Malmros et al. |
| 4,919,141 A | 4/1990 | Zier et al. |

(Continued)

FOREIGN PATENT DOCUMENTS

| | | |
|---|---|---|
| CA | 2312102 | 7/1999 |
| JP | 62-142888 | 6/1987 |

(Continued)

OTHER PUBLICATIONS

International Search Report for PCT/US03/06820 published Dec. 18, 2003.

(Continued)

*Primary Examiner* — Melanie Y Brown

(57) ABSTRACT

The present invention relates to methods for measuring an amount of an analyte using an electrochemical assay in a conduit comprising a sensor, wherein said sensor comprises an electrode having a surface layer of immobilized antibody that binds said analyte, and a counter/reference electrode disposed within said conduit. A solution comprising a substrate for said enzyme and at least one air segment contacts the sensor to remove unbound analyte and labeled antibody from a region of the sensor. The disclosed invention is adaptable to the point-of-care clinical diagnostic field, including use in accident sites, emergency rooms, surgery, nursing homes, intensive care units, and non-medical environments.

11 Claims, 9 Drawing Sheets

(56) References Cited

U.S. PATENT DOCUMENTS

| | | |
|---|---|---|
| 4,997,526 A | 3/1991 | Robblee |
| 5,073,484 A | 12/1991 | Swanson et al. |
| 5,096,669 A | 3/1992 | Lauks et al. |
| 5,183,740 A | 2/1993 | Ligler et al. |
| 5,200,051 A | 4/1993 | Cozzette et al. |
| 5,201,851 A | 4/1993 | Holmstrom |
| 5,229,297 A | 7/1993 | Schnipelsky et al. |
| 5,242,828 A | 9/1993 | Bergstrom |
| 5,254,479 A | 10/1993 | Chemelli |
| 5,313,264 A | 5/1994 | Ivarsson |
| 5,447,440 A | 9/1995 | Davis et al. |
| 5,503,985 A | 4/1996 | Cathey et al. |
| 5,628,961 A | 5/1997 | Davis et al. |
| 5,807,752 A | 9/1998 | Brizgys et al. |
| 5,821,399 A | 10/1998 | Zelin |
| 6,074,827 A | 6/2000 | Nelson et al. |
| 6,117,290 A | 9/2000 | Say et al. |
| 6,193,864 B1 | 2/2001 | Leader et al. |
| 6,221,238 B1 | 4/2001 | Grundig et al. |
| 6,251,615 B1 | 6/2001 | Oberhardt |
| 6,296,020 B1 | 10/2001 | McNeely et al. |
| 6,348,354 B1 | 2/2002 | Adolfsen et al. |
| 6,413,782 B1 | 7/2002 | Parce et al. |
| 6,438,498 B1 | 8/2002 | Opalsky et al. |
| 6,548,263 B1 | 4/2003 | Kapur et al. |
| 6,670,115 B1 * | 12/2003 | Zhang ............................ 435/5 |
| 6,783,649 B2 * | 8/2004 | Hedberg et al. ............ 204/603 |
| 7,169,358 B2 | 1/2007 | Henkens et al. |
| 2002/0055167 A1 | 5/2002 | Pouralunmadi et al. |
| 2002/0127602 A1 | 9/2002 | Shi et al. |
| 2002/0179439 A1 | 12/2002 | Weng et al. |
| 2003/0095897 A1 | 5/2003 | Grate et al. |
| 2006/0160205 A1 | 7/2006 | Blackburn et al. |

FOREIGN PATENT DOCUMENTS

| | | |
|---|---|---|
| JP | H04-501768 | 3/1992 |
| JP | H09-504372 | 4/1997 |
| JP | 11-247761 | 9/1999 |
| JP | 2001-65458 | 3/2001 |
| JP | 2002-31055 | 1/2002 |
| JP | 2002-161856 | 6/2002 |
| JP | 2002-266762 | 9/2002 |
| JP | 3392871 B2 | 3/2003 |
| JP | 3469585 B2 | 11/2003 |
| WO | WO 86/05590 A | 9/1986 |

OTHER PUBLICATIONS

International Search Report for International Application No. PCT/JP03/11996.
Office Action for Canadian Patent Application CA 2,478,608.
Eddowes, "Direct Immunochemical Sensing: Basic Chemical Principles and Fundamental Limitations", Biosensors, 3: 1-15, 1987.
Laurell, "Electroimmunoassay", Methods in Enzymology, vol. 73, Academic Press, New York, 339, 340, 346-348, 1981.
Green, "Electrochemical Immunoassays", Phil. Trans. R. Soc. London, 316: 135-142, 1987.
Office Action for Japanese Application 2003-575110 mailed Oct. 15, 2008.
European Office Action for European Application 03 716 329.2 mailed Jul. 2, 2007 (4 Pages).
International Search Report for PCT/JP03/11996 mailed on Dec. 9, 2003 (4 Pages).
Japanese Office Action for Japanese Application 2009-032424 mailed on Jan. 26, 2011 (4 Pages).

* cited by examiner

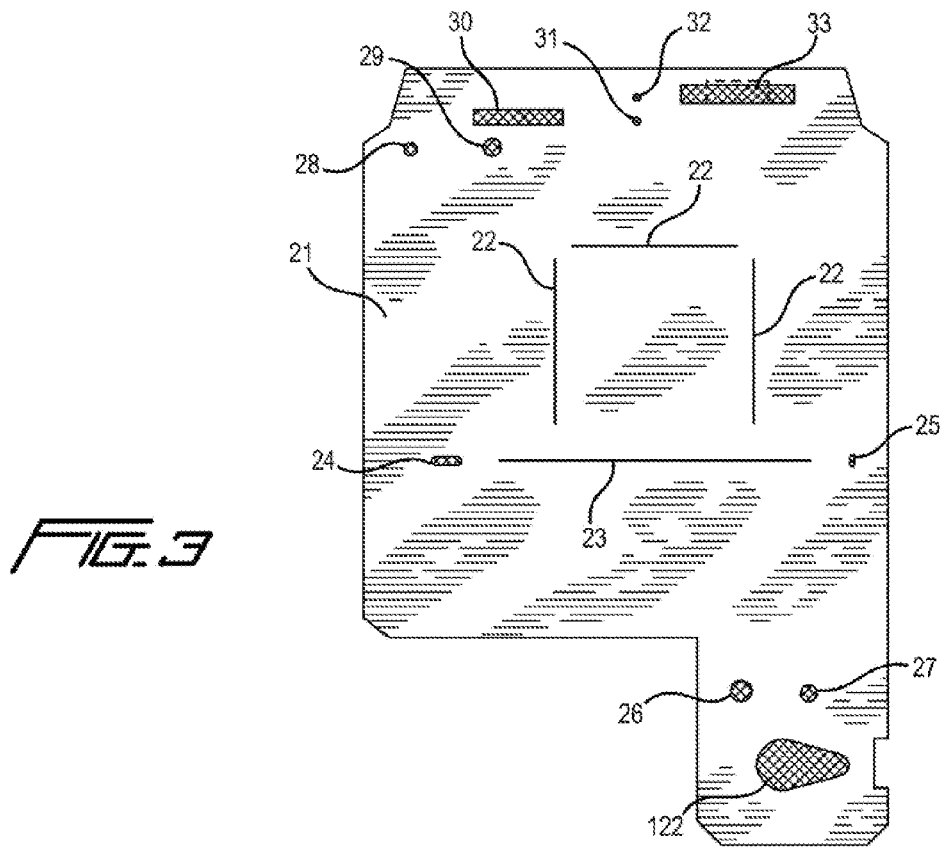
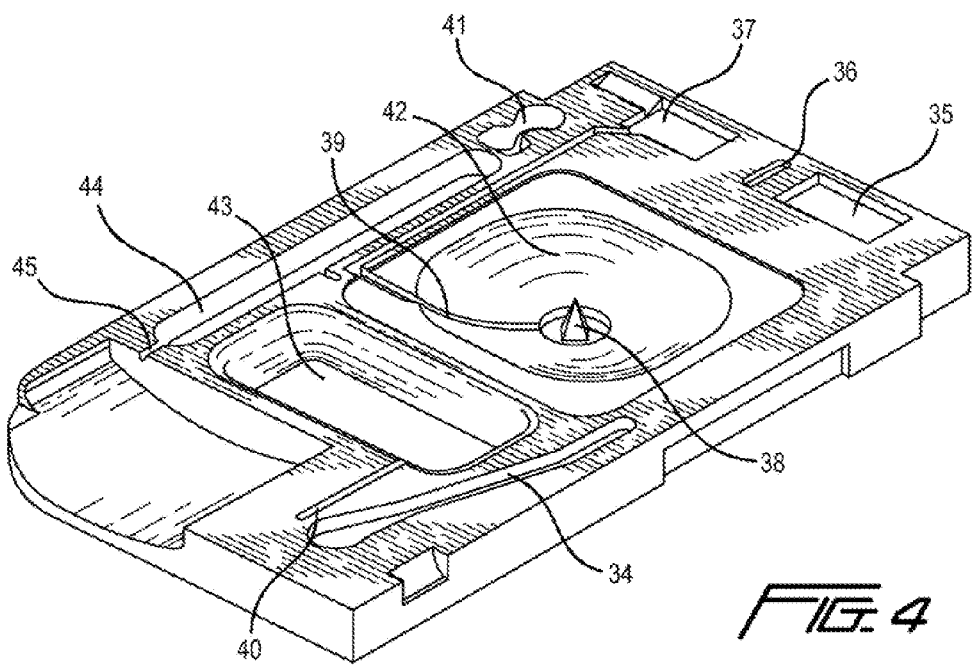

APPARATUS AND METHODS FOR ANALYTE MEASUREMENT AND IMMUNOASSAY

CROSS-REFERENCE TO RELATED APPLICATION

This application is a divisional of U.S. patent application Ser. No. 13/198,253, filed Aug. 8, 2011, now U.S. Pat. No. 8,222,024 which is a divisional of U.S. patent application Ser. No. 12/165,925, filed Jul. 1, 2008, now U.S. Pat. No. 8,017,382 which is a divisional application of U.S. patent application Ser. No. 10/087,730, filed Mar. 5, 2002, now U.S. Pat. No. 7,419,821, the entire contents of which are hereby incorporated by reference.

FIELD OF THE INVENTION

In its broadest aspect, the invention relates to an apparatus and method for rapid in situ determinations of analytes in liquid samples that is capable of being used, for example, in the point-of-care clinical diagnostic field, including use at accident sites, emergency rooms, in surgery, in intensive care units, and also in non-medical environments.

The present invention thus relates to an apparatus and its method of use for determining the presence and/or concentrations of analytes in a liquid sample. More particularly, the invention provides single-use disposable cartridges, adapted for conducting diverse real-time or near real-time assays of analytes. The invention further relates to a cartridge that provides novel features for processing a metered portion of a sample. The cartridge incorporates novel features for precise and flexible control of the movement of a sample or a second fluid within the cartridge, and for the optional amending of sample or fluid with one or more additional reagents or compounds during an assay. While the cartridges of the present invention are intended for use in a reading apparatus, they may also be used separately. They comprise conduits, pump means, a fluid, metering means, valves, and an optional sensor or sensors for determining the position or positions of liquids within the conduits. In specific embodiments, the invention relates to the determination of analytes in biological samples such as blood using electrochemical immunosensors or other ligand/ligand receptor-based biosensors. The invention further relates to a simplified construction of a biosensor, in particular for fabrication of electrochemical immunoassay biosensors capable of determining a wide range of analytes for which receptors or antibodies can be obtained.

BACKGROUND OF THE INVENTION

A multitude of laboratory tests for analytes of interest are performed on biological samples for diagnosis, screening, disease staging, forensic analysis, pregnancy testing, drug testing, and other reasons. While a few qualitative tests, such as pregnancy tests, have been reduced to simple kits for the patient's home use, the majority of quantitative tests still require the expertise of trained technicians in a laboratory setting using sophisticated instruments. Laboratory testing increases the cost of analysis and delays the results. In many circumstances, delay can be detrimental to a patient's condition or prognosis, such as for example the analysis of markers indicating of myocardial infarction. In these critical situations and others, it would be advantageous to be able to perform such analyses at the point of care, accurately, inexpensively, and with a minimum of delay.

A disposable sensing device for measuring analytes in a sample of blood is disclosed by Lauks in U.S. Pat. No. 5,096,669. Other devices are disclosed by Davis, et al. in U.S. Pat. Nos. 5,628,961 and 5,447,440 for a clotting time. The disclosed apparatuses comprise reading apparatus and a cartridge which fits into the reading apparatus for the purpose of measuring analyte concentrations and viscosity changes in a sample of blood as a function of time. A potential problem with disposable devices is variability of fluid test parameters from cartridge to cartridge due to manufacturing tolerances or machine wear. Zelin, U.S. Pat. No. 5,821,399 discloses methods to overcome this problem using automatic flow compensation controlled by a reading apparatus using conductimetric sensors located within a cartridge. U.S. Pat. Nos. 5,096,669, 5,628,961, 5,447,440, and 5,821,399 are hereby incorporated in their respective entireties by reference.

Antibodies are extensively used in the analysis of biological analytes. For a review of basic principles see Eddowes, *Biosensors* 3:1-15, 1987. While in all such applications an antibody provides analyte binding specificity, a variety of different analytical approaches have been employed to detect, either directly or indirectly, the binding of an antibody to its analyte. Various alternative assay formats (other than those used in typical research laboratories, such as Western blotting) have been adopted for quantitative immunoassay, which are distinguished from qualitative immunoassay kits, such as pregnancy testing kits. As an example of antibody use, Ligler, in U.S. Pat. No. 5,183,740 disclosed a flow-through immunosensor device comprising a column loaded with particles coated with an antibody bound to a labeled antigen. When a sample is flowed through the column, unlabeled antigen displaces labeled antigen which then flows to a detector. In an alternative approach, Giaever, in U.S. Pat. No. 4,018,886 discloses the use of magnetic particles coated with an antibody, which are first magnetically circulated in a sample to accelerate binding of the analyte, then concentrated in a small volume, and finally the antibody-antigen complex is cleaved from the bead to yield a concentrated solution of the complex. U.S. Pat. No. 5,073,484 to Swanson discloses a method in which a fluid-permeable solid medium has reaction zones through which a sample flows. A reactant that is capable of reaction with the analyte is bound to the solid medium in a zone. A localized, detectable product is produced in the zone when analyte is present. In a similar concept, U.S. Pat. No. 5,807,752 to Brizgys discloses a test system in which a solid phase is impregnated with a receptor for an analyte of interest. A second analyte-binding partner attached to a spectroscopically-determinable label and a blocking agent is introduced, and the spatial distribution of the label is measured. Spectroscopic measurements require a light transducer, typically a photomultiplier, phototransistor, or photodiode, and associated optics that may be bulky or expensive, and are not required in electrochemical methods, in which an electrical signal is produced directly.

Because a quantitative immunoassay typically requires multiple steps (e.g., a binding step followed by a rinse step with a solution that may or may not contain a second reagent), most of the foregoing methods are either operated manually, or require bulky machinery with complex fluidics. An example of the latter approach is provided in U.S. Pat. No. 5,201,851 which discloses methods providing complex fluidics for very small volumes on a planar surface. This method is used, for example, in the Biacore system (Pharmacia) which is housed in a bench-top instrument and uses surface plasmon resonance to detect binding of macromolecules to an immobilized receptor on a surface. See, U.S. Pat. Nos. 5,242,828 and 5,313,264.

The foregoing references disclose optical means for detecting the binding of an analyte to a receptor. Electrochemical detection, in which binding of an analyte directly or indirectly causes a change in the activity of an electroactive species adjacent to an electrode, has also been applied to immunoassay. For a review of electrochemical immunoassay, see: Lauren, et al., Methods in Enzymology, vol. 73, "*Electroimmunoassay*", Academic Press, New York, 339, 340, 346-348 (1981). For example, U.S. Pat. No. 4,997,526 discloses a method for detecting an analyte that is electroactive. An electrode poised at an appropriate electrochemical potential is coated with an antibody to the analyte. When the electroactive analyte binds to the antibody, a current flows at the electrode. This approach is restricted in the analytes that can be detected; only those analytes that have electrochemical midpoint potentials within a range that does not cause the electrode to perform non-specific oxidation or reduction of other species present in the sample by the electrode. The range of analytes that may be determined is extended by the method disclosed in U.S. Pat. No. 4,830,959, which is based upon enzymatic conversion of a non-mediator to a mediator. Application of the aforementioned invention to sandwich immunoassays, where a second antibody is labeled with an enzyme capable of producing mediator from a suitable substrate, means that the method can be used to determine electroinactive analytes.

Other electrical properties have also been employed in analyte sensors. U.S. Pat. Nos. 4,334,850 and 4,916,075 to Malmros disclose a polyacetylene film comprising an element whose electrical resistance varies in response to the presence of an analyte. Electric field effects are exploited in U.S. Pat. No. 4,238,757 to Schenck, where a field-effect transistor (FET) immunosensor is disclosed. An immunoassay based upon the use of an analyte labeled with a particle that affects the electrical reactance of an electrode is disclosed by Pace in U.S. Pat. No. 4,233,144. It will be apparent from these descriptions, that in each of the foregoing examples where other electrical properties are employed, the existence or magnitude of the required electrical property change may be different for each analyte. Therefore, there exists a need for assay techniques that can be automated and applied to diverse analytes to create assays with substantially uniform characteristics independent of specific characteristics of individual analyte species.

Microfabrication techniques (e.g., photolithography and plasma deposition) are attractive for construction of multilayered sensor structures in confined spaces. Methods for microfabrication of electrochemical immunosensors, for example on silicon substrates, are disclosed in U.S. Pat. No. 5,200,051 to Cozette, et al., which is hereby incorporated in its entirety by reference. These include dispensing methods, methods for attaching biological reagent, e.g., antibodies, to surfaces including photoformed layers and microparticle latexes, and methods for performing electrochemical assays.

In an electrochemical immunosensor, the binding of an analyte to its cognate antibody produces a change in the activity of an electroactive species at an electrode that is poised at a suitable electrochemical potential to cause oxidation or reduction of the electroactive species. There are many arrangements for meeting these conditions. For example, electroactive species may be attached directly to an analyte (see above), or the antibody may be covalently attached to an enzyme that either produces an electroactive species from an electroinactive substrate, or destroys an electroactive substrate. See, M. J. Green (1987) *Philos. Trans. R. Soc. Lond. B. Biol. Sci.* 316:135-142, for a review of electrochemical immunosensors.

Therefore, there exists within the field of analyte sensing, and in particular for applications in which analytes must be determined within biological samples such as blood, a need for apparatus that can rapidly and simply determine analytes at the point-of-care, and can be performed by less highly trained staff than is possible for conventional laboratory-based testing. Frequently, it would be of benefit in the diagnosis and treatment of critical medical conditions for the attending physician or nurse to be able to obtain clinical test results without delay. Furthermore, an improved apparatus should be adaptable to determination of a range of analytes and capable of single-use so that immediate disposal of the sample after testing minimizes the risk of biological or chemical contamination. These and other needs are met by the present invention as will become clear to one of skill in the art to which the invention pertains upon reading the following disclosure.

SUMMARY OF THE INVENTION

It is therefore an objective of the present invention to provide improved apparatus and methods for the determination of analytes in a liquid sample, which avoid the aforementioned disadvantages and drawbacks.

It is a further objective of the present invention to permit rapid, inexpensive, in situ determinations of analytes using a cartridge having an array of analyte sensors and means for sequentially presenting a sample and a fluid (amended or not) to the analyte array. The cartridges are designed to be preferably operated with a reading device, such as, for example, disclosed in U.S. Pat. No. 5,096,669 to Lauks, et al., issued Mar. 17, 1992, or U.S. Pat. No. 5,821,399 to Zelin, issued Oct. 13, 1998, which are hereby incorporated in their respective entireties by reference.

The present invention provides cartridges, and methods for their use, for the processing of liquid samples to determine the presence or amount of an analyte within the sample. In specific embodiments the cartridge contains a metering means, which permits an unmetered volume of a sample to be introduced into a cartridge and from which a metered amount can be processed by the cartridge and its associated reading apparatus. Thus the physician or operator is relieved of the task of accurately measuring the volume of sample prior to measurement, with consequent savings of time, effort, and also increased accuracy and reproducibility. In most specific embodiments, the metering means comprises an elongated sample chamber bounded by a capillary stop and having along its length an air entry point. Air pressure exerted at the air entry point drives a metered volume of the sample past the capillary stop. The metered volume is predetermined by the volume of the sample chamber between the air entry point and the capillary stop.

A cartridge according to the present invention has the advantage that the sample and a second fluid can contact the sensor array at different times during an assay sequence. The sample and second fluid may also be independently amended with other reagents or compounds present initially as dry coatings within the respective conduits. Controlled motion of the liquids within the cartridge further permits more than one substance to be amended into each liquid whenever the sample or fluid is moved to a new region of the conduit. In this way, provision is made for multiple amendments to each fluid, greatly extending the complexity of automated assays that can be performed, and therefore enhancing the utility of the present invention.

It is therefore an objective of the present invention to provide a flexible analyte analysis system, capable of adaptation to diverse assay protocols. Control of liquid motion is achieved through coordinated action of pump means, valves, conduit restrictions, air segments, and conductimetric and other sensors. The cartridge is intended for use in conjunction with a reading device, which coordinates liquid movements within the cartridge. Pump means are provided that apply pressure to displace sample and fluid through the conduits of the cartridge. Precise control of the movement of the sample and fluid is provided in some embodiments by one or more conductimetric sensors disposed within the conduits, which sense the presence or absence of a conductive fluid at particular points. This information is optionally used to control the pump means. In other embodiments, the cartridge further comprises valves that control the direction of sample and fluid movement. For example, in one embodiment a valve that closes after contact with a liquid enables one pump means to move both the sample and a second liquid sequentially over the analyte sensor array. Furthermore, in some embodiments, means are provided to introduce one or more air segments into the second conduit to segment the liquid therein and thus prevent mixing between segments.

In a disposable cartridge, the amount of liquid contained is preferably kept small to minimize cost and size. Therefore, in the present invention, segments within the conduits are also used to assist in cleaning and rinsing the conduits by passing the air-liquid interface of a segment over the sensor array or other region to be rinsed at least once. It has been surprisingly found that more efficient rinsing, using less fluid, is achieved by this method compared to continuous rinsing by a larger volume of fluid.

Restrictions within the conduits serve several purposes in the present invention. A capillary stop located between the sample chamber and first conduit is used to prevent displacement of a sample introduced into the holding chamber until sufficient pressure is applied to overcome the resistance of the capillary stop. A restriction within the second conduit is used to divert wash fluid along an alternative pathway towards the waste chamber when the fluid reaches the constriction. Small holes in the gasket, together with a hydrophobic coating, are provided to prevent flow from the first conduit to the second conduit until sufficient pressure is applied. Features that control the flow of liquids within and between the conduits of the present invention are herein collectively termed "valves." In these and other ways, the present invention has as an objective the provision of a flexible system adaptable to diverse assays, as will become evident to one of skill in the art upon reading the disclosure.

One embodiment of the invention, therefore, provides a single-use cartridge with a sample-holding chamber connected to a first conduit which contains an analyte sensor or array of analyte sensors. A second conduit, partly containing a fluid, is connected to the first conduit and air segments can be introduced into the fluid in the second conduit in order to segment it. Pump means are provided to displace the sample within the first conduit, and displaces fluid from the second conduit into the first conduit. Thus, the sensor or sensors can be contacted first by a sample and then by a second fluid.

A second embodiment of the cartridge includes a closeable valve located between the first conduit and a waste chamber. This embodiment permits displacement of the fluid from the second conduit into the first conduit using only a single pump means connected to the first conduit. This embodiment further permits efficient washing of the conduits of the cartridge of the present invention, which is an important feature of a small single-use cartridge. In operation, the sample is displaced to contact the sensors, and is then displaced through the closeable valve into the waste chamber. Upon wetting, the closeable valve seals the opening to the waste chamber, providing an airtight seal that allows fluid in the second conduit to be drawn into contact with the sensors using only the pump means connected to the first conduit. In this embodiment, the closeable valve permits the fluid to be displaced in this manner and prevents air from entering the first conduit from the waste chamber.

In a third embodiment, both a closeable valve and means for introducing segments into the conduit are provided. This embodiment has many advantages, among which is the ability to reciprocate a segmented fluid over the sensor or array of sensors. Thus a first segment or set of segments is used to rinse a sensor, and then a fresh segment replaces it for taking measurements. Only one pump means (that connected to the first conduit) is required.

In a fourth embodiment, which is the preferred embodiment, analyte measurements are performed in a thin-film of liquid coating an analyte sensor. Such thin-film determinations are preferably performed amperometrically. The cartridge of the preferred embodiment differs from the foregoing embodiments in having both a closeable valve that is sealed when the sample is expelled through the valve, and an air vent within the conduits that permits at least one air segment to be subsequently introduced into the measuring fluid, thereby increasing the efficiency with which the sample is rinsed from the sensor, and further permitting removal of substantially all the liquid from the sensor prior to measurement, and still further permitting segments of fresh liquid to be brought across the sensor to permit sequential, repetitive measurements for improved accuracy and internal checks of reproducibility.

The analysis scheme for the detection of low concentrations of immunoactive analyte relies on the formation of an enzyme labeled antibody/analyte/surface-bound antibody "sandwich" complex. The concentration of analyte in a sample is converted into a proportional surface concentration of an enzyme. The enzyme is capable of amplifying the analyte's chemical signal by converting a substrate to a detectable product. For example, where alkaline phosphatase is the enzyme, a single enzyme molecule can produce several thousand detectable molecules per minute, providing several orders of magnitude improvement in the detectability of the analyte compared to schemes in which an electroactive species is attached to the antibody in place of alkaline phosphatase.

In immunosensor embodiments, it is advantageous to contact the sensor first with a sample and then with a wash fluid prior to recording a response from the sensor. In specific embodiments, the sample is amended with an antibody-enzyme conjugate that binds to the analyte of interest within the sample before the amended sample contacts the sensor. Binding reactions in the sample produce an analyte/antibody-enzyme complex. The sensor comprises an immobilized antibody to the analyte, attached close to an electrode surface. Upon contacting the sensor, the analyte/antibody-enzyme complex binds to the immobilized antibody near the electrode surface. It is advantageous at this point to remove from the vicinity of the electrode as much of the unbound antibody-enzyme conjugate as possible to minimize background signal from the sensor. The enzyme of the antibody-enzyme complex is advantageously capable of converting a substrate, provided in the fluid, to produce an electrochemically active species. This active species is produced close to the electrode and provides either a current from a redox reaction at the electrode when a suitable potential is applied (amperometric operation). Alternatively, if the electroactive species is an ion, it can be measured potentiometrically. In amperometric measurements the potential may either be fixed during the measurement, or varied according to a predetermined waveform.

For example, a triangular wave can be used to sweep the potential between limits, as is used in the well-known technique of cyclic voltammetry. Alternatively, digital techniques such as square waves can be used to improve sensitivity in detection of the electroactive species adjacent to the electrode. From the current or voltage measurement, the amount or presence of the analyte in the sample is calculated. These and other analytical electrochemical methods are well known in the art.

In embodiments in which the cartridge comprises an immunosensor, the immunosensor is advantageously microfabricated from a base sensor of an unreactive metal such as gold, platinum or iridium, which is overlaid with a bioactive layer attached to a microparticle, for example latex particles. The microparticles are dispensed onto the electrode surface, forming an adhered, porous bioactive layer. The bioactive layer has the property of binding specifically to the analyte of interest, or of manifesting a detectable change when the analyte is present, and is most preferably an immobilized antibody directed against the analyte.

In operation, therefore, one goal of the present invention is to provide an immunosensor cartridge that is preferably operated in a basic sense as follows. (However, the invention is not restricted to embodiments comprising an immunosensor, but includes any ligand-receptor interaction.) An unmetered amount of a preferably biological sample is placed into the sample chamber of the cartridge, and the cartridge is placed into a reading apparatus. A metered portion of the sample is amended with at least one antibody-enzyme conjugate, and is then contacted with the immunosensor. A second fluid, which contains an electroinactive substrate for the enzyme, is used to rinse the immunosensor substantially free of unbound antibody-enzyme conjugate, and the electrical response of the immunosensor electrode is recorded and analyzed for the presence, or amount of, the analyte of interest. The cartridge may contain a plurality of immunosensors and reagents.

After the reading, the operator removes and discards the cartridge. The reader is then ready for another measurement. While the use of the invention will frequently be referred to in a biological or medical context, it will be appreciated that the present invention may be practiced in any situation where it is desired to perform in situ chemical analyses of liquid samples at speeds which approach real-time.

A further object of the invention is to provide a novel means of making an electrochemical measurement in a conduit, whereby an immunosensor is exposed to sample and a fluid containing a substrate, after which the fluid is removed from the conduit except for a thin layer of fluid on the wall of the conduit in the vicinity of the sensor.

While the invention is described in terms of an immunoassay cartridge application, the invention is envisaged as containing within its scope other clinical chemical assays known in the art.

BRIEF DESCRIPTION OF THE DRAWINGS

These and other objectives, features and advantages of the present invention are described in the following detailed description of the specific embodiments and are illustrated in the following figures in which:

FIG. 3 is a top view of the layout of a tape gasket for an immunosensor cartridge.

FIG. 4 is an isometric top view of an immunosensor cartridge base.

FIG. 9 is a top view of the mask design for the conductimetric and immunosensor electrodes for an immunosensor cartridge.

DETAILED DESCRIPTION OF THE EMBODIMENTS

In Section A, a description of specific embodiments of the immunosensor of the present invention is provided together with three EXAMPLES of their use. In Section B, the preferred embodiment is described, together with one EXAMPLE of its use.

A. Specific Embodiments

Figure 1:
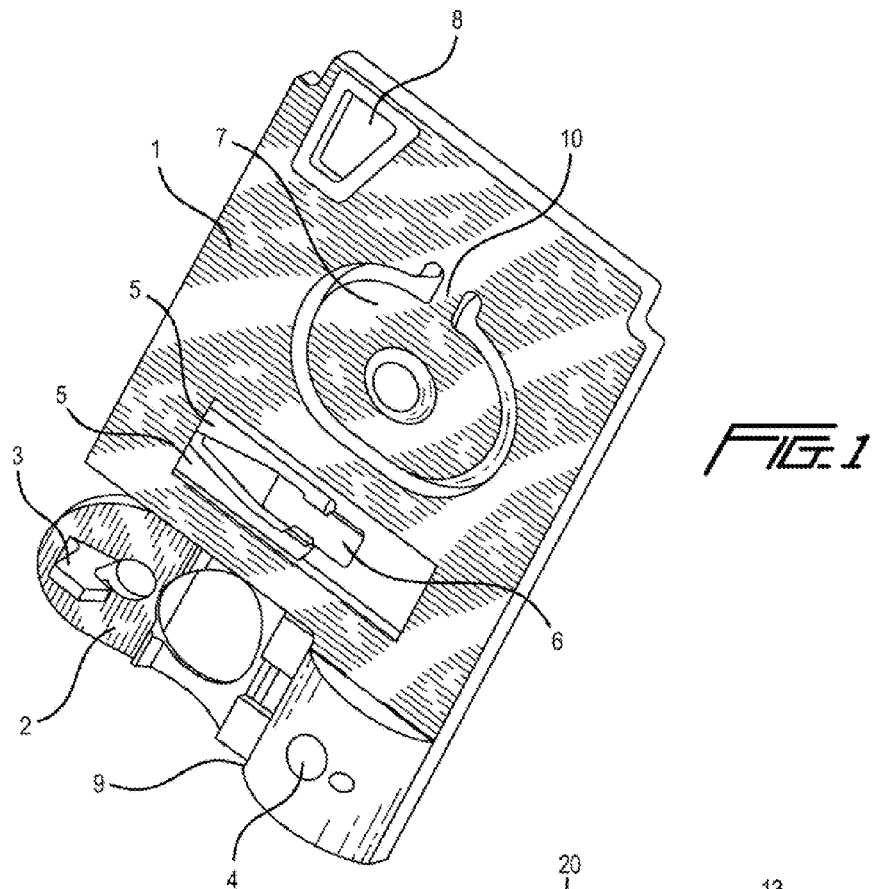
FIG. 1 is an isometric top view of an immunosensor cartridge cover.

Cartridge Construction:
Referring to the figures, the cartridge of the present invention comprises a cover, FIGS. 1, 2, a base, FIG. 4, and a thin-film adhesive gasket, FIG. 3, disposed between the base and the cover. Referring now to FIG. 1, the cover 1 is made of a rigid material, preferably plastic, capable of repetitive deformation at flexible hinge regions 5, 9, 10 without cracking. The cover comprises a lid 2, attached to the main body of the cover by a flexible hinge 9. In operation, after introduction of a sample into the sample holding chamber 34, the lid can be secured over the entrance to the sample entry port 4, preventing sample leakage, and the lid is held in place by hook 3. The cover further comprises two paddles 6, 7, that are moveable relative to the body of the cover, and which are attached to it by flexible hinge regions 5, 10. In operation, when operated upon by a pump means, paddle 6 exerts a force upon an air bladder comprised of cavity 43, which is covered by thin-film gasket 21, to displace fluids within conduits of the cartridge. When operated by a second pump means, paddle 7 exerts a force upon the gasket 21, which can deform because of slits 22 cut therein. The cartridge is adapted for insertion into a reading apparatus, and therefore has a plurality of mechanical and electrical connections for this purpose. It should also be apparent that manual operation of the cartridge is possible. Thus, upon insertion of the cartridge into a reading apparatus, the gasket transmits pressure onto a fluid-containing foil pack filled with approximately 130 uL of analysis/wash solution ("fluid") located in cavity 42, rupturing the package upon spike 38, and expelling fluid into conduit 39, which is connected via a short transecting conduit in the base to the sensor conduit. The analysis fluid fills the front of the analysis conduit first pushing fluid onto a small opening in the tape gasket that acts as a capillary stop. Other motions of the analyzer mechanism applied to the cartridge are used to inject one or more segments into the analysis fluid at controlled positions within the analysis conduit. These segments are used to help wash the sensor surface and the surrounding conduit with a minimum of fluid.

The cover further comprises a hole covered by a thin pliable film 8. In operation, pressure exerted upon the film expels one or more air segments into a conduit 20 through a small hole 28 in the gasket.

Figure 2:
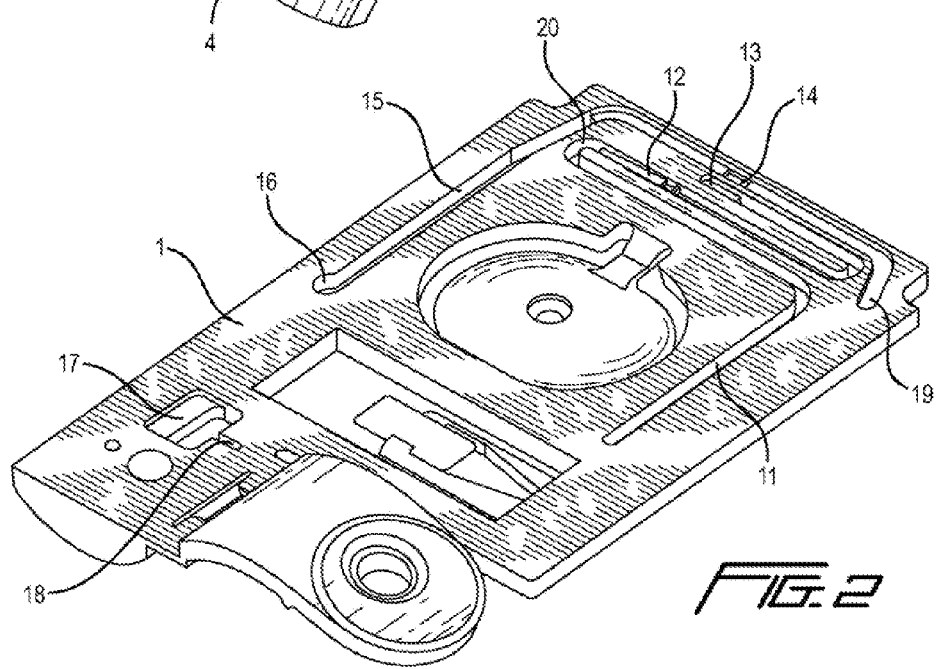
FIG. 2 is an isometric bottom view of an immunosensor cartridge cover.

Referring to FIG. 2, the lower surface of the base further comprises second conduit 11, and first conduit 15. Second conduit 11 includes a constriction 12, which controls fluid flow by providing resistance to the flow of a fluid. Optional coatings 13, 14 provide hydrophobic surfaces, which together with gasket holes 31, 32, control fluid flow between conduits 11, 15. A recess 17 in the base provides a pathway for air in conduit 34 to pass to conduit 34 through hole 27 in the gasket.

Referring to FIG. 3, thin-film gasket 21 comprises various holes and slits to facilitate transfer of fluid between conduits within the base and the cover, and to allow the gasket to deform under pressure where necessary. Thus, hole 24 permits fluid to flow from conduit 11 into waste chamber 44; hole 25 comprises a capillary stop between conduits 34 and 11; hole 26 permits air to flow between recess 18 and conduit 40; hole 27 provides for air movement between recess 17 and conduit 34; and hole 28 permits fluid to flow from conduit 19 to waste chamber 44 via optional closeable valve 41. Holes 30 and 33 permit the plurality of electrodes that are housed within cutaways 35 and 37, respectively, to contact fluid within conduit 15. In a specific embodiment, cutaway 37 houses a ground electrode, and/or a counter-reference electrode, and cutaway 35 houses at least one analyte sensor and, optionally, a conductimetric sensor.

Referring to FIG. 4, conduit 34 is the sample holding chamber that connects the sample entry port 4 to first conduit 11 in the assembled cartridge. Cutaway 35 houses the analyte sensor or sensors, or an analyte responsive surface, together with an optional conductimetric sensor or sensors. Cutaway 37 houses a ground electrode if needed as a return current path for an electrochemical sensor, and may also house an optional conductimetric sensor. Cutaway 36 provides a fluid path between gasket holes 31 and 32 so that fluid can pass between the first and second conduits. Recess 42 houses a fluid-containing package, e.g., a rupturable pouch, in the assembled cartridge that is pierced by spike 38 because of pressure exerted upon paddle 7 upon insertion into a reading apparatus. Fluid from the pierced package flows into the second conduit at 39. An air bladder is comprised of recess 43 which is sealed on its upper surface by gasket 21. The air bladder is one embodiment of a pump means, and is actuated by pressure applied to paddle 6 which displaces air in conduit 40 and thereby displaces the sample from sample chamber 34 into first conduit 15.

The location at which air enters the sample chamber (gasket hole 27) from the bladder, and the capillary stop 25, together define a predetermined volume of the sample chamber. An amount of the sample corresponding to this volume is displaced into the first conduit when paddle 6 is depressed. This arrangement is therefore one possible embodiment of a metering means for delivering a metered amount of an unmetered sample into the conduits of the cartridge.

In the present cartridge, a means for metering a sample segment is provide in the base plastic part. The segment size is controlled by the size of the compartment in the base and the position of the capillary stop and air pipe holes in the tape gasket. This volume can be readily varied from 2 to 200 microliters. Expansion of this range of sample sizes is possible within the context of the present invention.

The fluid is pushed through a pre-analytical conduit 11 that can be used to amend a reagent (e.g., particles or soluble molecules) into the sample prior to its presentation at the sensor conduit 19. Alternatively, the amending reagent may be located in portion 15, beyond portion 16. Pushing the sample through the pre-analytical conduit also serves to introduce tension into the diaphragm pump paddle 7 which improves its responsiveness for actuation of fluid displacement.

In some assays, metering is advantageous if quantitation of the analyte is required. A waste chamber is provided, 44, for sample and/or fluid that is expelled from the conduit, to prevent contamination of the outside surfaces of the cartridge. A vent connecting the waste chamber to the external atmosphere is also provided, 45. A feature of the cartridge is that once a sample is loaded, analysis can be completed and the cartridge discarded without the operator or others contacting the sample.

Figure 5:
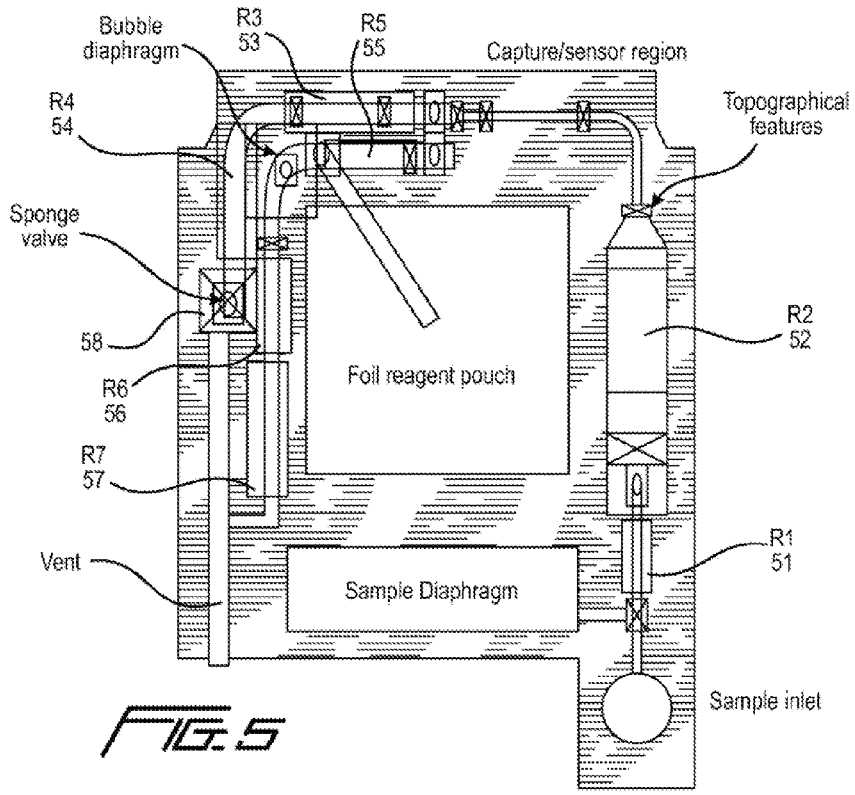
FIG. 5 is a schematic view of the layout of an immunosensor cartridge.

Referring now to FIG. 5, a schematic diagram of the features of a cartridge and components is provided, wherein 51-57 are portions of the conduits and sample chamber that can optionally be coated with dry reagents to amend a sample or fluid. The sample or fluid is passed at least once over the dry reagent to dissolve it. Reagents used to amend samples or fluid within the cartridge include antibody-enzyme conjugates, or blocking agents that prevent either specific or non-specific binding reactions among assay compounds. A surface coating that is not soluble but helps prevent non-specific adsorption of assay components to the inner surfaces of the cartridges can also be provided.

Within a segment of sample or fluid, an amending substance can be preferentially dissolved and concentrated within a predetermined region of the segment. This is achieved through control of the position and movement of the segment. Thus, for example, if only a portion of a segment, such as the leading edge, is reciprocated over the amended substance, then a high local concentration of the substance can be achieved close to the leading edge. Alternatively, if an homogenous distribution of the substance is desired, for example if a known concentration of an amending substance is required for a quantitative analysis, then further reciprocation of the sample or fluid will result in mixing and an even distribution.

In specific embodiments, a closeable valve is provided between the first conduit and the waste chamber. In one embodiment, this valve, 58, is comprised of a dried sponge material that is coated with an impermeable substance. In operation, contacting the sponge material with the sample or a fluid results in swelling of the sponge to fill the cavity 41, thereby substantially blocking further flow of liquid into the waste chamber 44. Furthermore, the wetted valve also blocks the flow of air between the first conduit and the waste chamber, which permits the first pump means connected to the sample chamber to displace fluid within the second conduit, and to displace fluid from the second conduit into the first conduit in the following manner. After the sample is exposed to the sensor for a controlled time, the sample is moved into the post-analytical conduit 19 where it can be amended with another reagent. It can then be moved back to the sensor and a second reaction period can begin. Alternately, the post-analysis conduit can serve simply to separate the sample segment from the sensor. Within this post-analysis conduit is a single closeable valve which connects the air vent of the sensor conduit to the diaphragm air pump. When this valve closes, the sample is locked in the post analytical conduit and cannot be moved back to the sensor chip. There are several different design examples for this valve that are encompassed within the present invention. Some designs are activated mechanically while others activate on liquid contact. Other types of closeable valve that are encompassed by the present invention include, but are not limited to; a flexible flap held in an open position by a soluble glue or a gelling polymer that dissolves or swells upon contact with a fluid or sample thus causing the flap to close; and alternatively, in one specific embodiment, a thin layer of a porous paper or similar material interposed between a conduit and either the waste chamber or ambient air such that the paper is permeable to air while dry but impermeable when wet. In the latter case it is not necessary that the closeable valve be interposed between a conduit and the waste chamber: the valve passes little to no liquid before closing and so the valve is appropriately placed when positioned between a conduit and the ambient air surrounding the cartridge. In practical construction, a piece of filter paper is placed on an opening in the tape gasket in the fluid path to be controlled. Air can readily move through this media to allow fluid to be moved through the fluid path. When the fluid is pushed over this filter, the filter media becomes filled with liquid and further motion through the fluid path is stopped. Once the filter become wet, significant pressures would be required to move liquid through the pores of the filter. Air flow through the filter is also prevented because of the higher pressure required to push the liquid out of the filter. This valve embodiment requires very little liquid to actuate the valve, and actuation occurs rapidly and reliably. Materials, their dimensions, porosity, wettability, swelling characteristics and related parameters are selected to provide for rapid closure, within one second or more slowly, e.g., up to 60 seconds, after first contacting the sample, depending on the specific desired closure time.

Alternatively, the closeable valve is a mechanical valve. In this embodiment, a latex diaphragm is placed in the bottom of the air bladder on top of a specially constructed well. The well contains two openings which fluidically connect the air vent to the sample conduit. As the analyzer plunger pushes to the bottom of the air bladder, it presses on this latex diaphragm which is adhesive backed and seals the connection between the two holes. This blocks the sample's air vent, locking the sample in place.

Figure 6:
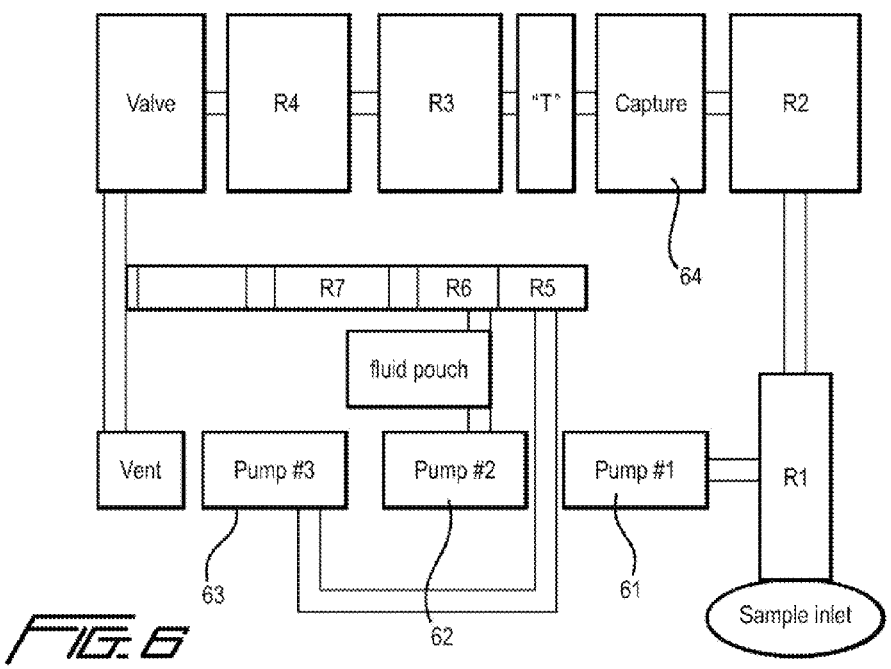
FIG. 6 is a schematic view of the fluid and air paths within an immunosensor cartridge, including sites for amending fluids with dry reagents.

Referring now to FIG. 6, which illustrates the schematic layout of an immunosensor cartridge, there are provided three pump means, 61-63. While these pumps have been described in terms of specific embodiments, it will be readily understood that any pump means capable of performing the respective functions of pump means 61-63 may be used within the present invention. Thus, pump means 1, 61, must be capable of displacing the sample from the sample holding chamber into the first conduit; pump means 2, 62, must be capable of displacing fluid within the second conduit; and pump means 3, 63, must be capable of inserting at least one segment into the second conduit. Other types of pump which are envisaged in the present application include, but are not limited to, an air sac contacting a pneumatic means whereby pressure is applied to said air sac, a flexible diaphragm, a piston and cylinder, an electrodynamic pump, and a sonic pump. With reference to pump means 3, 63, the term "pump means" includes all methods by which one or more segments are inserted into the second conduit, such as a pneumatic means for displacing air from an air sac, a dry chemical that produces a gas when dissolved, or a plurality of electrolysis electrodes operably connected to a current source. In a specific embodiment, the segment is produced using a mechanical segment generating diaphragm that may have more than one air bladder or chamber. The well 8 has a single opening which connects the inner diaphragm pump and the fluid filled conduit into which a segment is to be injected 20. The diaphragm can be segmented to produce multiple segments, each injected in a specific location within a fluid filled conduit.

In alternative embodiments, a segment is injected using a passive feature. A well in the base of the cartridge is sealed by tape gasket. The tape gasket covering the well has two small holes on either end. One hole is open while the other is covered with a filter material which wets upon contact with a fluid. The well is filled with a loose hydrophilic material such as a cellulose fiber filter, paper filter or glass fiber filter. This hydrophilic material draws the liquid into the well in the base via capillary action, displacing the air which was formerly in the well. The air is expelled through the opening in the tape gasket creating a segment whose volume is determined by the volume of the well and the volume of the loose hydrophilic material. The filter used to cover one of the inlets to the well in the base can be chosen to meter the rate at which the fluid fills the well and thereby control the rate at which the segment is injected into the conduit in the cover. This passive feature permits any number of controlled segments to be injected at specific locations within a fluid path and requires a minimum of space.

The present invention will be better understood with reference to the specific embodiments set forth in the following examples.

EXAMPLE 1

Figure 7:
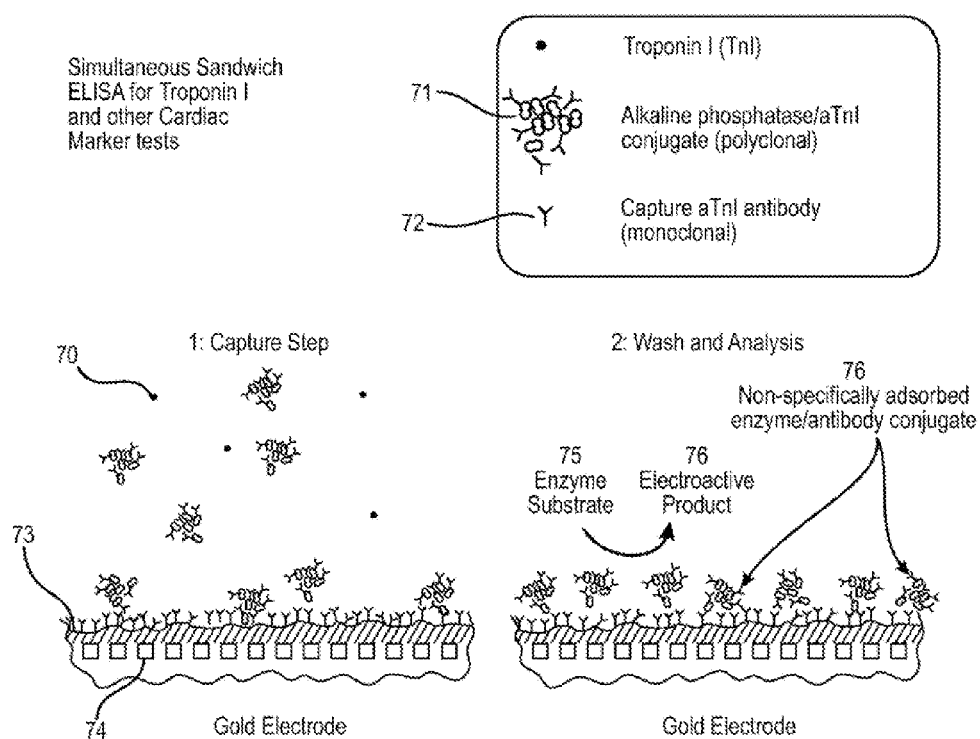
FIG. 7 illustrates the principle of operation of an electrochemical immunosensor.

Referring now to FIG. 7, which illustrates the principle of an amperometric immunoassay according to specific embodiments of the present invention for determination of troponin I (TnI), a marker of cardiac function. A blood sample, for example, is introduced into the sample holding chamber of a cartridge of the present invention, and is amended by a conjugate molecule comprising alkaline phosphatase enzyme (AP) covalently attached to a polyclonal anti-troponin I antibody (aTnI) 71. This conjugate specifically binds to the TnI, 70, in the blood sample, producing a complex made up of TnI bound to the AP-aTnI conjugate. In a capture step, this complex binds to the capture aTnI antibody 72 attached on, or close to, the immunosensor. The sensor chip has a conductivity sensor which is used to monitor when the sample reaches the sensor chip. The time of arrival of the fluid can be used to detect leaks within the cartridge; a delay in arrival signals a leak. The position of the sample segment within the sensor conduit can be actively controlled using the edge of the fluid as a marker. As the sample/air interface crosses the conductivity sensor, a precise signal is generated which can be used as a fluid marker from which controlled fluid excursions can be executed. The fluid segment is preferentially oscillated edge-to-edge over the sensor in order to present the entire sample to the sensor surface. A second reagent can be introduced in the sensor conduit beyond the sensor chip, which becomes homogenously distributed during the fluid oscillations.

The sensor chip contains a capture region or regions coated with antibodies for the analyte of interest. These capture regions are defined by a hydrophobic ring of polyimide or another photolithographically produced layer. A microdroplet or several microdroplets (approximately 5-40 nanoliters in size) containing antibodies in some form, for example bound to latex microspheres, is dispensed on the surface of the sensor. The photodefined ring contains this aqueous droplet allowing the antibody coated region to be localized to a precision of a few microns. The capture region can be made from 0.03 to roughly 2 square millimeters in size. The upper end of this size is limited by the size of the conduit and sensor in present embodiments, and is not a limitation of the invention.

Thus, the gold electrode 74 is coated with a biolayer 73 comprising a covalently attached anti-troponin I antibody, to which the TnI/AP-aTnI complex binds. AP is thereby immobilized close to the electrode in proportion to the amount of TnI initially present in the sample. In addition to specific binding, the enzyme-antibody conjugate may bind non-specifically to the sensor. Non-specific binding provides a background signal from the sensor that is undesirable and preferably is minimized. As described above, the rinsing protocols, and in particular the use of segmented fluid to rinse the sensor, provide efficient means to minimize this background signal. In a second step subsequent to the rinsing step, a substrate 75 that is hydrolyzed by, for example, alkaline phosphatase to produce an electroactive product 76 is presented to the sensor. In specific embodiments the substrate is comprised of a phosphorylated ferrocene or p-aminophenol. The amperometric electrode is either clamped at a fixed electrochemical potential sufficient to oxidize or reduce a product of the hydrolyzed substrate but not the substrate directly, or the potential is swept one or more times through an appropriate range. Optionally, a second electrode may be coated with a layer where the complex of TnI/AP-aTnI is made during manufacture, to act as a reference sensor or calibration means for the measurement.

In the present example, the sensor comprises two amperometric electrodes which are used to detect the enzymatically produced 4-aminophenol from the reaction of 4-aminophenylphosphate with the enzyme label alkaline phosphatase. The electrodes are preferably produced from gold surfaces coated with a photodefined layer of polyimide. Regularly spaced opening in the insulating polyimide layer define a grid of small gold electrodes at which the 4-aminophenol is oxidized in a 2 electron per molecule reaction. Sensor electrodes further comprise a biolayer, while reference electrodes can be constructed, for example, from gold electrodes lacking a biolayer, or from silver electrodes, or other suitable material. Different biolayers can provide each electrode with the ability to sense a different analyte.

$$H_2N-C_6H_4-OH \rightarrow HN=C_6H_4=O+2H^++2e^-$$

Substrates, such as p-aminophenol species, can be chosen such that the E of the substrate and product differ substantially. Preferably, the $E_{1/2}$ of the substrate is substantially higher than that of the product. When the condition is met, the product can be selectively electrochemically measured in the presence of the substrate.

The size and spacing of the electrode play an important role in determining the sensitivity and background signal. The important parameters in the grid are the percentage of exposed metal and the spacing between the active electrodes. The position of the electrode can be directly underneath the antibody capture region or offset from the capture region by a controlled distance. The actual amperometric signal of the electrodes depends on the positioning of the sensors relative to the antibody capture site and the motion of the fluid during the analysis. A current at the electrode is recorded that depends upon the amount of electroactive product in the vicinity of the sensor.

The detection of alkaline phosphatase activity in this example relies on a measurement of the 4-aminophenol oxidation current. This is achieved at a potential of about +60 mV versus the Ag/AgCl ground chip. The exact form of detection used depends on the sensor configuration. In one version of the sensor, the array of gold microelectrodes is located directly beneath the antibody capture region. When the analysis fluid is pulled over this sensor, enzyme located on the capture site converts the 4-aminophenylphosphate to 4-aminophenol in an enzyme limited reaction. The concentration of the 4-aminophenylphosphate is selected to be in excess, e.g., 10 times the Km value. The analysis solution is 0.1 M in diethanolamine, 1.0 M NaCl, buffered to a pH of 9.8. Additionally, the analysis solution contains 0.5 mM MgCl which is a cofactor for the enzyme.

In another electrode geometry embodiment, the electrode is located a few hundred microns away from the capture region. When a fresh segment of analysis fluid is pulled over the capture region, the enzyme product builds with no loss due to electrode reactions. After a time, the solution is slowly pulled from the capture region over the detector electrode resulting in a current spike from which the enzyme activity can be determined.

An important consideration in the sensitive detection of alkaline phosphatase activity is the non-4-aminophenol current associated with background oxidations and reductions occurring at the gold sensor. Gold sensors tend to give significant oxidation currents in basic buffers at these potentials. The background current is largely dependent on the buffer concentration, the area of the gold electrode (exposed area), surface pretreatments and the nature of the buffer used. Diethanolamine is a particularly good activating buffer for alkaline phosphatase. At molar concentrations, the enzymatic rate is increased by about three times over a non-activating buffer such as carbonate.

In alternative embodiments, the enzyme conjugated to an antibody or other analyte-binding molecule is urease, and the substrate is urea. Ammonium ions produced by the hydrolysis of urea are detected in this embodiment by the use of an ammonium sensitive electrode. Ammonium-specific electrodes are well-known to those of skill in the art. A suitable microfabricated ammonium ion-selective electrode is disclosed in U.S. Pat. No. 5,200,051, incorporated herein by reference. Other enzymes that react with a substrate to produce an ion are known in the art, as are other ion sensors for use therewith. For example, phosphate produced from an alkaline phosphatase substrate can be detected at a phosphate ion-selective electrode.

Figure 8:
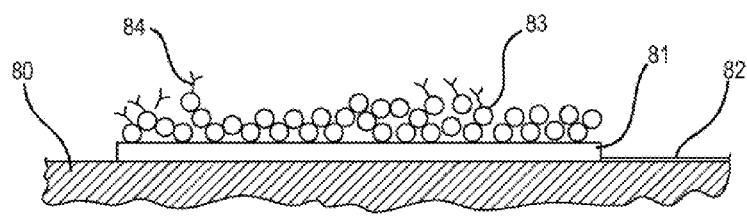
FIG. 8 is a side view of the construction of an electrochemical immunosensor with antibody-labeled particles not drawn to scale.
Figure 8:
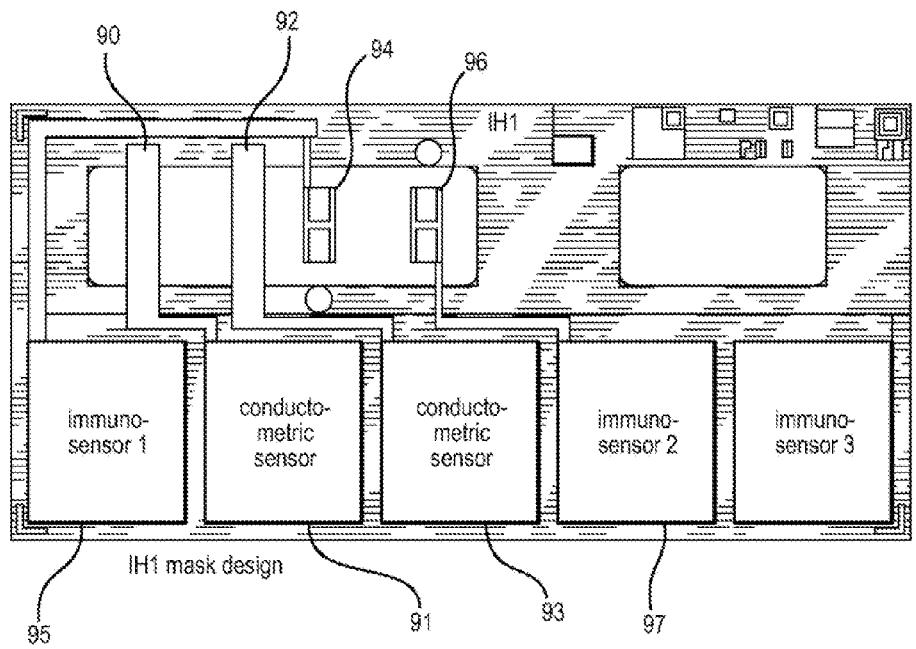

Referring now to FIG. 8, there is illustrated the construction of an embodiment of a microfabricated immunosensor. Preferably a planar non-conducting substrate is provided, 80, onto which is deposited a conducting layer 81 by conventional means or microfabrication known to those of skill in the art. The conducting material is preferably a noble metal such as gold or platinum, although other unreactive metals such as iridium may also be used, as may non-metallic electrodes of graphite, conductive polymer, or other materials. An electrical connection 82 is also provided. A biolayer 83 is deposited onto at least a portion of the electrode. In the present disclosure, a biolayer means a porous layer comprising on its surface a sufficient amount of a molecule 84 that can either bind to an analyte of interest, or respond to the presence of such analyte by producing a change that is capable of measurement. Optionally, a permselective screening layer may be interposed between the electrode and the biolayer to screen electrochemical interferents as described in U.S. Pat. No. 5,200,051.

In specific embodiments, a biolayer is constructed from latex beads of specific diameter in the range of about 0.001 to 50 microns. The beads are modified by covalent attachment of any suitable molecule consistent with the above definition of a biolayer. Many methods of attachment exist in the art, including providing amine reactive N-hydroxysuccinimide ester groups for the facile coupling of lysine or N-terminal amine groups of proteins. In specific embodiments, the biomolecule is chosen from among ionophores, cofactors, polypeptides, proteins, glycopeptides, enzymes, immunoglobulins, antibodies, antigens, lectins, neurochemical receptors, oligonucleotides, polynucleotides, DNA, RNA, or suitable mixtures. In most specific embodiments, the biomolecule is an antibody selected to bind one or more of human chorionic gonadotrophin, troponin I, troponin T, troponin C, a troponin complex, creatine kinase, creatine kinase subunit M, creatine kinase subunit B, myoglobin, myosin light chain, or modified fragments of these. Such modified fragments are generated by oxidation, reduction, deletion, addition or modification of at least one amino acid, including chemical modification with a natural moiety or with a synthetic moiety. Preferably, the biomolecule binds to the analyte specifically and has an affinity constant for binding analyte ligand of about $10^7$ to $10^{15}$ $M^{-1}$.

In one embodiment, the biolayer, comprising beads having surfaces that are covalently modified by a suitable molecule, is affixed to the sensor by the following method. A microdispensing needle is used to deposit onto the sensor surface a small droplet, preferably about 0.4 nl, of a suspension of modified beads. The droplet is permitted to dry, which results in a coating of the beads on the surface that resists displacement during use.

In addition to immunosensors in which the biolayer is in a fixed position relative to an amperometric sensor, the present invention also envisages embodiments in which the biolayer is coated upon particles that are mobile. The cartridge can contain mobile microparticles capable of interacting with an analyte, for example magnetic particles that are localized to an amperometric electrode subsequent to a capture step, whereby magnetic forces are used to concentrate the particles at the electrode for measurement. One advantage of mobile microparticles in the present invention is that their motion in the sample or fluid accelerates binding reactions, making the capture step of the assay faster. For embodiments using non-magnetic mobile microparticles, a porous filter is used to trap the beads at the electrode.

Referring now to FIG. 9, there is illustrated a mask design for several electrodes upon a single substrate. By masking and etching techniques, independent electrodes and leads can be deposited. Thus, a plurality of immunosensors, 94 and 96, and conductimetric sensors, 90 and 92, are provided in a compact area at low cost, together with their respective connecting pads, 91, 93, 95, and 97, for effecting electrical connection to the reading apparatus. In principle, a very large array of sensors can be assembled in this way, each sensitive to a different analyte or acting as a control sensor.

Specifically, immunosensors are prepared as follows. Silicon wafers are thermally oxidized to form approximately a 1 micron insulating oxide layer. A titanium/tungsten layer is sputtered onto the oxide layer to a preferable thickness of between 100-1000 Angstroms, followed by a layer of gold that is most preferably 800 Angstroms thick. Next, a photoresist is spun onto the wafer and is dried and baked appropriately. The surface is then exposed using a contact mask, such as a mask corresponding to that illustrated in FIG. 9. The latent image is developed, and the wafer is exposed to a gold-etchant. The patterned gold layer is coated with a photodefinable polyimide, suitably baked, exposed using a contact mask, developed, cleaned in an $O_2$ plasma, and preferably imidized at 350° C. for 5 hours. The surface is then printed with antibody-coated particles. Droplets, preferably of about 0.4 nl volume and containing 2% solid content in deionized water, are deposited onto the sensor region and are dried in place by air drying. Optionally, an antibody stabilization reagent (e.g., Stabilicoat, obtained from SurModica Corp.) is overcoated onto the sensor.

Drying the particles causes them to adhere to the surface in a manner that prevents dissolution in either sample or fluid containing a substrate. This method provides a reliable and reproducible immobilization process suitable for manufacturing sensor chips in high volume.

Figure 10:
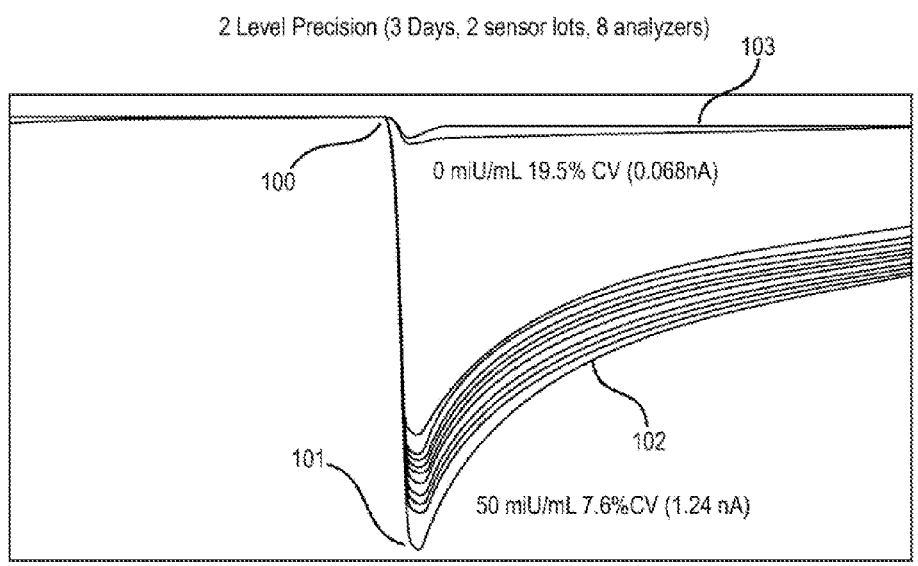
FIG. 10 illustrates the electrochemical responses of immunosensors constructed with an anti-HCG antibody when presented with 50 mU/mL, of HCG.
Figure 13:
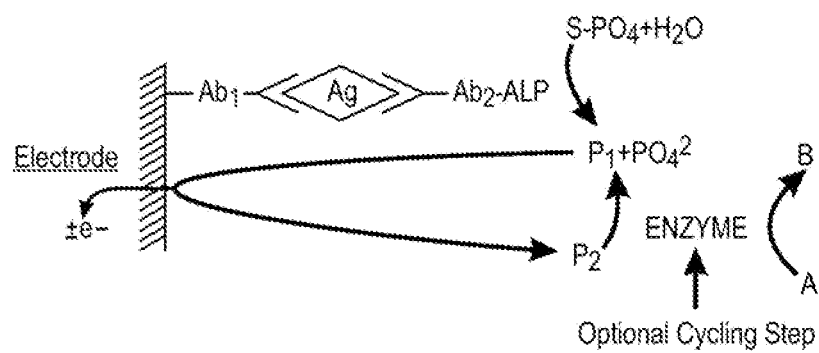
FIG. 13 is a schematic illustration of enzymatic regeneration of an electroactive species.

Referring now to FIG. 10, there are illustrated results obtained for analysis of samples containing 0 or 50 miU/mL, human chorionic gonadotrophin (HCG) and an HCG-sensitive amperometric immunosensor. At time 100, a solution containing a p-aminophenol phosphate is supplied to a sensor which is previously treated with HCG and an anti-HCG polyclonal antibody conjugated to alkaline phosphatase. As the substrate is hydrolyzed by alkaline phosphatase, a current increases to a maximum 101, and thereafter declines 102, as substrate within the diffusion volume of the sensor is depleted and oxidized p-aminophenol accumulates. Good reproducibility is obtained between sensors, as shown by the output signal characteristics of individual single-use sensors. In operation, displacement of the fluid containing the enzyme substrate provides fresh substrate to the electrode surface, and also removes products, so that multiple readings are easily obtained for a single sample. In an alternative embodiment, the signal at the electrode is augmented by enzymatic regeneration of the electroactive species in the vicinity of the electrode. In a specific embodiment, a phosphorylated ferrocene is used as the substrate for alkaline phosphatase attached to the antibody. Hydrolysis yields a ferrocene product, which is oxidized and detected at the electrode. In a second step, glucose oxidase enzyme and glucose are used to re-reduce the electrochemically oxidized ferrocene, with a consequent increase in the current and detection sensitivity. Referring now to FIG. 13, an electrode 130 oxidizes or reduces the electroactive product 132 of alkaline phosphatase immobilized as a complex 131 on or close to the electrode surface. In a second step, the electroactive species 132 is regenerated from the product 133 by the catalytic action of enzyme 134. This cycling reaction increases the concentration of electroactive species 132 in proximity to the electrode surface 130, and thereby increases the current recorded at the electrode.

Figure 11:
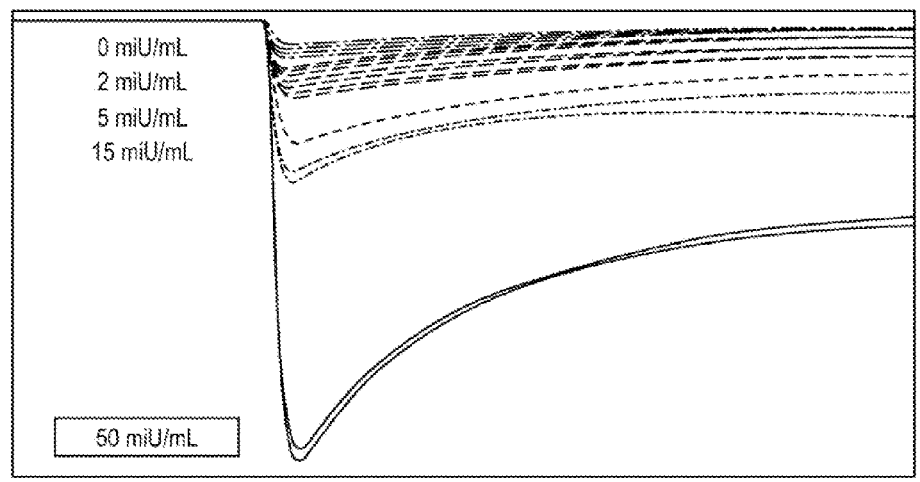
FIG. 11 illustrates the electrochemical response (current versus time) of an immunosensor constructed with an anti-HCG antibody when presented with various amounts of HCG from 0 to 50 mU/mL.
Figure 12:
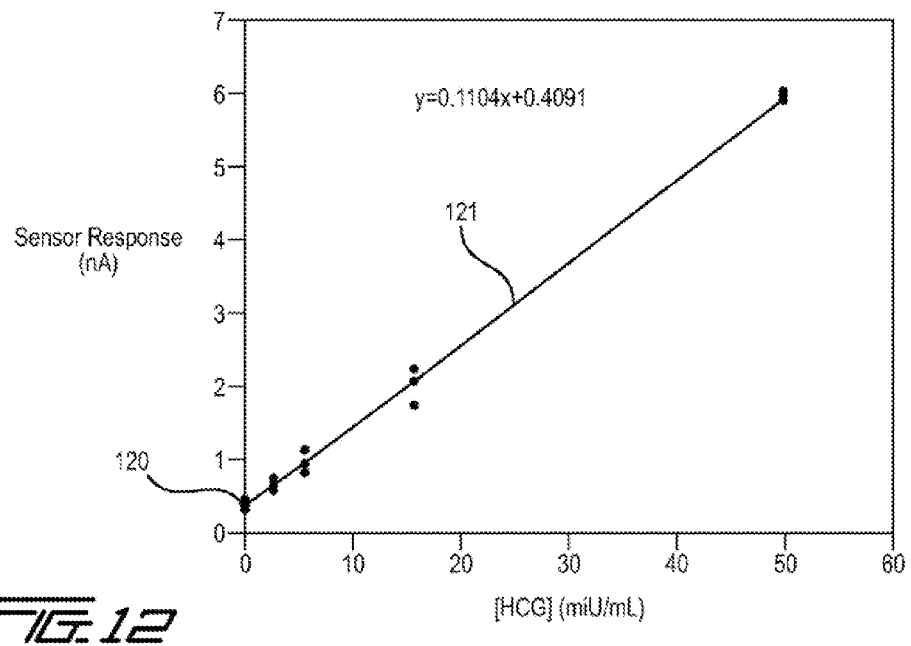
FIG. 12 illustrates the maximum current obtained when an immunosensor constructed with an anti-HCG antibody is presented with various amounts of HCG.

Referring now to FIG. 11, there is shown dose-response results obtained using HCG and an HCG-responsive amperometric immunosensor. Amounts of HCG equivalent to 0 to 50 miU/mL are allowed to bind to the immobilized antibody attached to the electrode, as in FIG. 10. Referring now to FIG. 12, good linearity, 121 of the response of the peak sensor current with increasing HCG is found. Thus, it is demonstrated that this embodiment can precisely and rapidly quantify HCG in a sample.

EXAMPLE 2

Method of Use a Cartridge of Claim 1

In a first cartridge embodiment, one exemplary analyte assay protocol using a cartridge of claim 1 is described. An unmetered fluid sample is introduced into sample chamber 34 of a cartridge according to claim 1, through sample entry port 4. Capillary stop 25 prevents passage of the sample into conduit 11 at this stage, and conduit 34 is filled with the sample. Lid 2 is closed to prevent leakage of the sample from the cartridge. The cartridge is then inserted into a reading apparatus, such as that disclosed in U.S. Pat. No. 5,821,399 to Zelin, which is hereby incorporated by reference. Insertion of the cartridge into a reading apparatus activates the mechanism which punctures a fluid-containing package located at 42 when the package is pressed against spike 38. Fluid is thereby expelled into the second conduit, arriving in sequence at 39, 20, 12 and 11. The constriction at 12 prevents further movement of fluid because residual hydrostatic pressure is dissipated by the flow of fluid via second conduit portion 11 into the waste chamber 44. In a second step, operation of a pump means applies pressure to air-bladder 43, forcing air through conduit 40, through cutaways 17 and 18, and into conduit 34 at a predetermined location 27. Capillary stop 25 and location 27 delimit a metered portion of the original sample. While the sample is within sample chamber 34, it is optionally amended with a compound or compounds present initially as a dry coating on the inner surface of the chamber. The metered portion of the sample is then expelled through the capillary stop by air pressure produced within air bladder 43. The sample passes into conduit 15 and into contact with the analyte sensor or sensors located within cutaway 35.

In embodiments employing an immunosensor located within cutout 35, the sample is amended prior to arriving at the sensor by, for example, an enzyme-antibody conjugate. An antibody that binds the analyte of interest is covalently attached to an enzyme that can generate a redox active substance close to an amperometric electrode. In specific embodiments, the enzyme may be alkaline phosphatase, which hydrolyzes certain organophosphate compounds, such as derivatives of p-aminophenol that liberate redox-active compounds when hydrolyzed. However, any enzyme capable of producing, destroying, or altering any compound that may be detected by a sensor may be employed in conjunction with a matching sensor. For example, antibody-urease conjugate may be used together with an ammonium sensor. Thus, the enzyme-antibody conjugate or conjugates amends the sample and binds to the analyte of interest. The immunosensor can comprise immobilized antibody that binds to an analyte of interest. When the amended sample passes over the immunosensor, the analyte of interest binds to the sensor, together with antibody-enzyme conjugate to which it is attached.

To promote efficient binding of the analyte to the sensor, the sample containing the analyte is optionally passed repeatedly over the sensor in an oscillatory motion. Preferably, an oscillation frequency of between about 0.2 and 2 Hz is used, most preferably 0.7 Hz. Thus enzyme is brought into close proximity to the amperometric electrode surface in proportion to the amount of analyte present in the sample.

Once an opportunity for the analyte/enzyme-antibody conjugate complex to bind to the immunosensor has been provided, the sample is ejected by further pressure applied to air bladder 43, and the sample passes to waste chamber 44.

A wash step next removes non-specifically bound enzyme-conjugate from the sensor chamber. Fluid in the second conduct is moved by a pump means 43, into contact with the sensors. The analysis fluid is pulled slowly until the first air segment is detected at a conductivity sensor.

Figure 14:
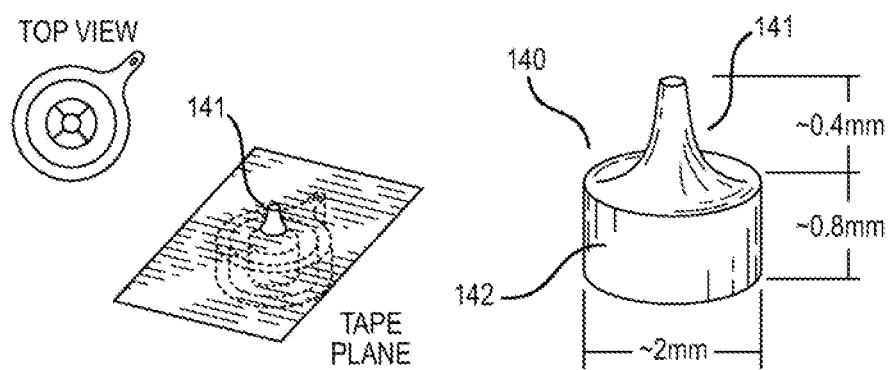
FIG. 14 illustrates segment forming means.

The air segment or segment can be produced within a conduit by any suitable means, including but not limited to, passive means, as shown in FIG. 14 and described below; active means including a transient lowering of the pressure within a conduit using pump means whereby air is drawn into the conduit through a flap or valve; or by dissolving a compound pre-positioned within a conduit that liberates a gas upon contacting fluid in the conduit, where such compound may be a carbonate, bicarbonate or the like. This segment is extremely effective at clearing the sample-contaminated fluid from conduit 15. The efficiency of the rinsing of the sensor region is greatly enhanced by the introduction of one or more air segments into the second conduit as described. The leading and/or trailing edges of air segments are passed one or more times over the sensors to rinse and resuspend extraneous material that may have been deposited from the sample. Extraneous material includes any material other than specifically bound analyte or analyte/antibody-enzyme conjugate complex. However, it is an object of the invention that the rinsing is not sufficiently protracted or vigorous as to promote dissociation of specifically bound analyte or analyte/antibody-enzyme conjugate complex from the sensor.

A second advantage of introducing air segments into the fluid is to segment the fluid. For example, after a first segment of the fluid is used to rinse a sensor, a second segment is then placed over the sensor with minimal mixing of the two segments. This feature further reduces background signal from the sensor by more efficiently removing unbound antibody-enzyme conjugate. After the front edge washing, the analysis fluid is pulled slowly until the first air segment is detected at a conductivity sensor. This segment is extremely effective at clearing the sample-contaminated fluid which was mixed in with the first analysis fluid sample.

A second advantage of introducing air segments into conduit two is to segment the fluid. For example, after a first segment of the fluid is used to rinse a sensor, a second segment is then placed over the sensor with minimal mixing of the two segments. This feature further reduces background signal from the sensor by more efficiently removing unbound antibody-enzyme conjugate.

For measurement, a new portion of fluid is placed over the sensors, and the current or potential, as appropriate to the mode of operation, is recorded as a function of time.

EXAMPLE 3

Method of Use of the Cartridge of Claim 2

The cartridge of claim 2 comprises all the elements of the cartridge of claim 1 together with a closeable valve, preferably located between the sensor chamber and the waste chamber. The method of use of the cartridge of claim 2 is herein illustrated by a specific embodiment in which the concentration of HCG is determined within a blood sample, which is introduced into the sample chamber of said cartridge. In the following time sequence, time zero (t=0) represents the time at which the cartridge is inserted into the cartridge reading device. Times are given in minutes. Between t=0 and t=1.5, the cartridge reading device makes electrical contact with the sensors through pads 91, 93, 95, and 97, and performs certain diagnostic tests. Insertion of the cartridge perforates the foil pouch introducing fluid into the second conduit as previously described. The diagnostic tests determine whether fluid or sample is present in the conduits using the conductivity electrodes; determine whether electrical short circuits are present in the electrodes; and ensure that the sensor and ground electrodes are thermally equilibrated to, preferably, 37° C. prior to the analyte determination.

Between t=1.5 and t=6.75, a metered portion of the sample, preferably between 4 and 200 µl, more preferably between 4 and 20 µl, and most preferably 7 µl, is used to contact the sensor as described in EXAMPLE 2. The edges defining the forward and trailing edges of the sample are reciprocally moved over the sensor region at a frequency that is preferably between 0.2 to 2.0 Hz, and is most preferably 0.7 Hz. During this time, the enzyme-antibody conjugate dissolves within the sample, as previously described. The amount of enzyme-antibody conjugate that is coated onto the conduit is selected to yield a concentration when dissolved that is preferably higher than the highest anticipated HCG concentration, and is most preferably six times higher than the highest anticipated HCG concentration in the sample.

Between t=6.75 and t=10.0 the sample is moved into the waste chamber via closeable valve 41, wetting the closeable valve and causing it to close as previously described. The seal created by the closing of the valve permits the first pump means to be used to control motion of fluid from conduit 11 to conduit 15. After the valve closes and the any remaining sample is locked in the post analysis conduit, the analyzer plunger retracts from the flexible diaphragm of the pump mean creating a partial vacuum in the sensor conduit. This forces the analysis fluid through the small hole in the tape gasket 31 and into a short transecting conduit in the base, 13, 14. The analysis fluid is pulled further and the front edge of the analysis fluid is oscillated across the surface of the sensor chip in order to shear the sample near the walls of the conduit. A conductivity sensor on the sensor chip is used to control this process. The efficiency of the process is monitored using the amperometric sensors through the removal of unbound enzyme-antibody conjugate which enhances the oxidation current measured at the electrode when the enzyme substrate, 4-aminophenyl phosphate is also present. The amperometric electrodes are polarized to 0.06 V versus the silver chloride reference-ground electrode. In this embodiment, the fluid is composed of a 0.1 M diethanolamine buffer, pH 9.8, with 1 mM $MgCl_2$, 1.0 M NaCl, 10 mM 4-aminophenylphosphate, and 10 µM NaI. The efficiency of the wash is optimally further enhanced by introduction into the fluid of one or more segments that segment the fluid within the conduit as previously described. The air segment may be introduced by either active or passive means. Referring now to FIG. 14, there is illustrated the construction of a specific means for passively introducing an air segment into said fluid. Within the base of the immunosensor is recess 140 comprising a tapered portion 141 and a cylindrical portion that are connected. The tapered portion is in fluid connection with a hole 142 of similar diameter in the tape gasket (FIG. 3) that separates the base (FIG. 4) and cover (FIGS. 1 and 2) of the assembled immunosensor cartridge. The recess contains an absorbent material that, upon contact with fluid, withdraws a small quantity of fluid from a conduit thereby passively introducing an air segment into the conduit. The volume of the recess and the amount and type of material within it may be adjusted to control the size of the air segment introduced. Specific materials include, but are not limited to, glass filter, a laminate comprising a 3 micron Versapor filter bonded by sucrose to a 60% viscose chiffon layer.

Fluid is forcibly moved towards sensor chip by the partial vacuum generated by reducing the mechanical pressure exerted upon paddle 6, causing the "T" region of the sensor channel in the vicinity of the transecting conduit to fill with analysis fluid. The T region of the sensor channel optionally has a higher channel height resulting a meniscus with a smaller radius of curvature. Further away from the T region towards the post-analytical conduit, the conduit height is optionally smaller. The analysis fluid passively flows from the T region towards this low conduit height region washing the conduit walls. This passive leak allows further effective washing of the T region using a minimal volume of fluid.

In this simple embodiment, the fluid located within the second conduit contains a substrate for the enzyme. In other embodiments, amendment of the fluid using dried substrate within the second conduit may be used.

Following the positioning of a final segment of fluid over the sensor, measurement of the sensor response is recorded and the concentration of analyte determined as described for EXAMPLE 2. Specifically, at least one sensor reading of a sample is made by rapidly placing over the sensor a fresh portion of fluid containing a substrate for the enzyme. Rapid displacement both rinses away product previously formed, and provides now substrate to the electrode. Repetitive signals are averaged to produce a measurement of higher precision, and also to obtain a better statistical average of the baseline, represented by the current immediately following replacement of the solution over the sensor.

B. Preferred Embodiment

Figure 15:
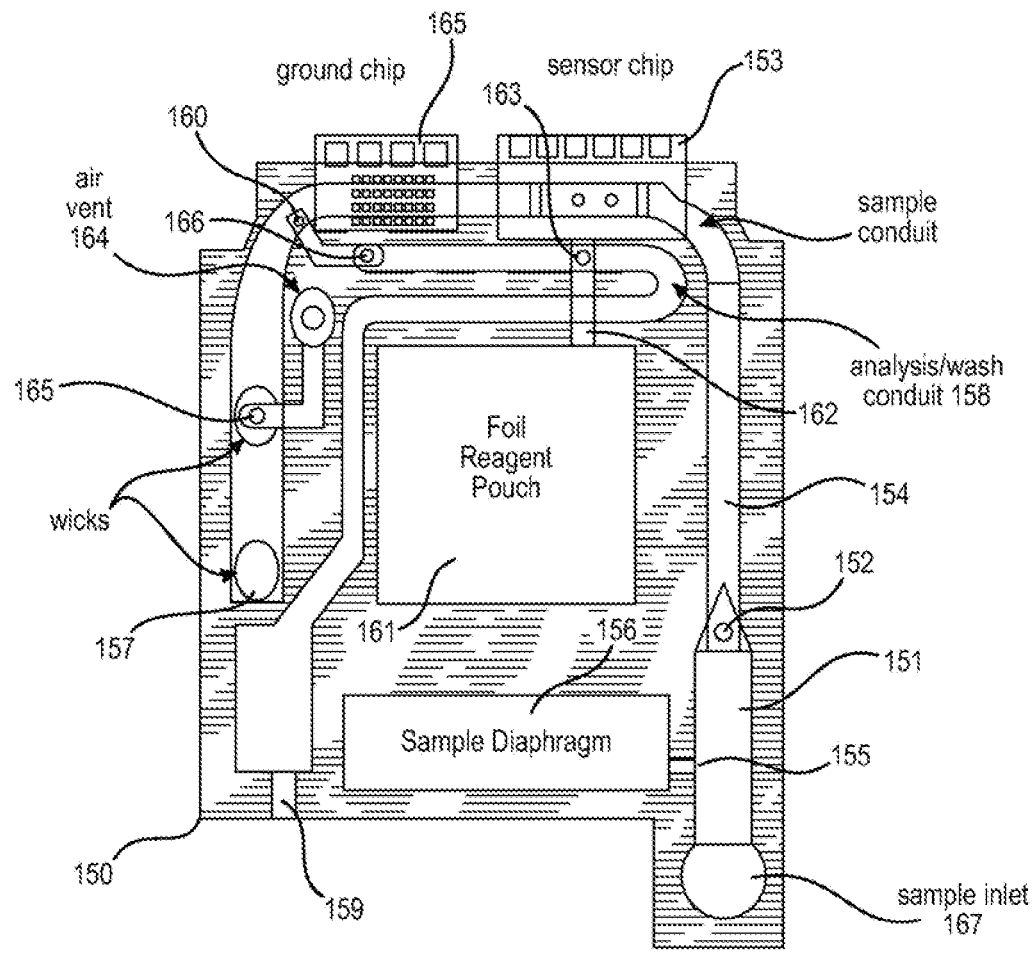
FIG. 15 is a top view of the preferred embodiment of an immunosensor cartridge.

Cartridge Construction and Operation:

Referring now to FIG. 15, there is shown a top view of the preferred embodiment of an immunosensor cartridge. The preferred embodiment differs from the specific embodiments of Section A in certain features and methods of use that are advantageous for the rapid, reproducible, and inexpensive determination of analytes. The preferred embodiment cartridge shares many features in common with the specific embodiment cartridges described above, and are therefore described with emphasis on specific differences. One skilled in the art to which the invention pertains will readily appreciate from the combined descriptions of Sections A and B the construction and use of the preferred embodiment.

The preferred embodiment cartridge 150 comprises a base and a top portion, preferably constructed of a plastic. The two portions are connected by a thin, adhesive gasket or thin pliable film. As in previous embodiments, the assembled cartridge comprises a sample chamber 151 into which a sample containing an analyte of interest is introduced via a sample inlet 152. A metered portion of the sample is delivered to the sensor chip 153, via the sample conduit 154 (first conduit) as before by the combined action of a capillary stop 152, preferably formed by a 0.012" laser cut hole in the gasket or film that connects the two portions of the cartridge, and an entry point 155 located at a predetermined point within the sample chamber whereby air introduced by the action of a pump means, such as a paddle pushing upon a sample diaphragm 156. After contacting the sensor to permit binding to occur, the sample is moved to vent 157, which contains a wicking material that absorbs the sample and thereby seals the vent closed to the further passage of liquid or air. The wicking material is preferably a cotton fiber material, a cellulose material, or other hydrophilic material having pores. It is important in the present application that the material is sufficiently absorbent (i.e., possesses sufficient wicking speed) that the valve closes within a time period that is commensurate with the subsequent withdrawal of the sample diaphragm actuating means described below, so that sample is not subsequently drawn back into the region of the sensor chip.

As in the specific embodiments, there is provided a wash conduit (second conduit) 158, connected at one end to a vent 159 and at the other end to the sample conduit at a point 160 of the sample conduit that is located between vent 157 and sensor chip 153. Upon insertion of the cartridge into a reading apparatus, a fluid is introduced into conduit 158. Preferably, the fluid is present initially within a foil pouch 161 that is punctured by a pin when an actuating means applies pressure upon the pouch. There is also provided a short conduit 162 that connects the fluid to conduit 154 via a small opening in the gasket 163. A second capillary stop initially prevents the fluid from reaching capillary stop 160, so that the fluid is retained within conduit 158.

After vent 157 has closed, the pump means is actuated, creating a lowered pressure within conduit 154. Air vent 164, preferably comprising a small flap cut in the gasket or a membrane that vibrates to provide an intermittent air stream, provides a means for air to enter conduit 158 via a second vent 165. The second vent 165 preferably also contains wicking material capable of closing the vent if wetted, which permits subsequent depression of sample diaphragm 156 to close vent 165, if required. Simultaneously with the actuation of sample diaphragm 156, fluid is drawn from conduit 158, through capillary stop 160, into conduit 154. Because the flow of fluid is interrupted by air entering vent 164, at least one air segment (a segment or stream of segments) is introduced.

Further withdrawal of sample diaphragm 156 draws the liquid containing at least one air segment back across the sensing surface of sensor chip 153. The presence of air-liquid boundaries within the liquid enhances the rinsing of the sensor chip surface to remove remaining sample. Preferably, the movement of the sample diaphragm 156 is controlled in conjunction with signals received from the conductivity electrodes housed within the sensor chip adjacent to the analyte sensors. In this way, the presence of liquid over the sensor is detected, and multiple readings can be performed by movement of the fluid in discrete steps.

It is advantageous in this preferred embodiment to perform analyte measurements when only a thin film of fluid coats the sensors, ground chip 165, and a contiguous portion of the wall of conduit 154 between the sensors and ground electrode. A suitable film is obtained by withdrawing fluid by operation of the sample diaphragm 156, until the conductimetric sensor located next to the sensor indicates that bulk fluid is no longer present in that region of conduit 154. It has been found that measurement can be performed at very low (nA) currents, the potential drop that results from increased resistance of a thin film between ground chip and sensor chip (compared to bulk fluid), is not significant.

The ground chip 165 is preferably silver/silver chloride. It is advantageous, to avoid air segments, which easily form upon the relatively hydrophobic silver chloride surface, to pattern the ground chip as small regions of silver/silver chloride interspersed with more hydrophilic regions, such as a surface of silicon dioxide. Thus, a preferred ground electrode configuration comprises an array of silver/silver chloride squares densely arranged and interspersed with silicon dioxide. There is a further advantage in the avoidance of unintentional segments if the regions of silver/silver chloride are somewhat recessed.

Figure 16:
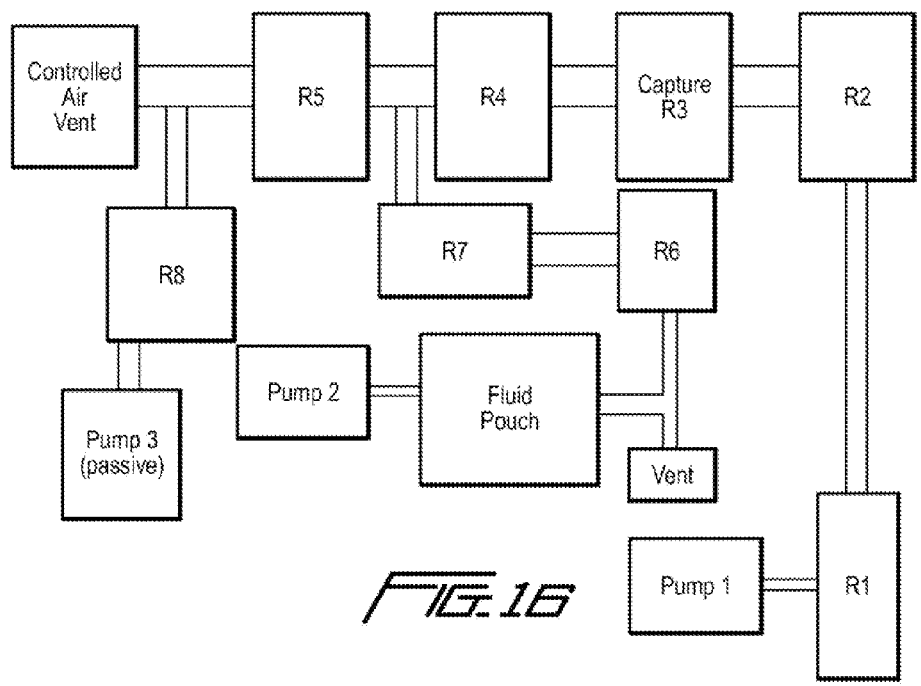
FIG. 16 is a schematic view of the fluidics of the preferred embodiment of an immunosensor cartridge.

Referring now to FIG. 16, there is shown a schematic view of the fluidics of the preferred embodiment of an immunosensor cartridge. Regions R1-R7 represent specific regions of the conduits associated with specific operational functions. Thus R1 represents the sample chamber; R2 the sample conduit whereby a metered portion of the sample is transferred to the capture region, and in which the sample is optionally amended with a substance coated upon the walls of the conduit; R3 represents the capture region, which houses the conductimetric and analyte sensors; R4 and R5 represent portions of the first conduit that are optionally used for further amendment of fluids with substances coated onto the conduit wall, whereby more complex assay schemes are achieved; R6 represents the portion of the second conduit into which fluid is introduced upon insertion of the cartridge into a reading apparatus; R7 comprises a portion of the conduit located between capillary stops 160 and 166, in which further amendment can occur; and R8 represents the portion of conduit 154 located between point 160 and vent 157, and which can further be used to amend liquids contained within.

EXAMPLE 4

Coordination of Fluidics and Analyte Measurement in a Cartridge of the Preferred Embodiment The use of the preferred embodiment immunocartridge is illustrate in this example. In the analysis sequence, a user places a sample into the cartridge, places the cartridge into the analyzer and in 1 to 20 minutes, a quantitative measurement of one or more analytes is performed. Herein is a non-limiting example of a sequence of events that occur during the analysis:

1) A 25 to 50 uL sample is introduced in the sample inlet 167 and fills to a capillary stop 151 formed by a 0.012" laser cut hole in the adhesive tape holding the cover and base components together. The user rotates a latex rubber disk mounted on a snap flap to close the sample inlet 167 and places the cartridge into the analyzer.

2) The analyzer makes contact with the cartridge, and a motor driven plunger presses onto the foil pouch 161 forcing the wash/analysis fluid out into a central conduit 158.

3) A separate motor driven plunger contacts the sample diaphragm 156 pushing a measured segment of the sample along the sample conduit (from reagent region R1 to R2). The sample is detected at the sensor chip 153 via the conductivity sensors. The sensor chip is located in capture region R3.

4) The sample is oscillated by means of the sample diaphragm 156 between R2 and R5 in a predetermined and controlled fashion for a controlled time to promote binding to the sensor.

5) The sample is pushed towards the waste region of the cartridge (R8) and comes in contact with a passive pump 157 in the form of a cellulose or similar absorbent wick. The action of wetting this wick seals the wick to air flow thus eliminating its ability to vent excess pressure generated by the sample diaphragm 156. The active vent becomes the "controlled air vent" of FIG. 16.

6) Rapid evacuation of the sample conduit (effected by withdrawing the motor driven plunger from the sample diaphragm 156) forces a mixture of air (from the vent) and wash/analysis fluid from the second conduit to move into the inlet located between R5 and R4 in FIG. 16. By repeating the rapid evacuation of the sample conduit, a series of air separated fluid segments are generated which are pulled across the sensor chip towards the sample inlet (from R4 to R3 to R2 and R1). This washes the sensor free of excess reagents and wets the sensor with reagents appropriate for the analysis. The wash/analysis fluid which originates in the foil pouch can be further amended by addition of reagents in R7 and R6 within the central wash/analysis fluid conduit.

7) The wash/analysis fluid segment is drawn at a slower speed towards the sample inlet to yield a sensor chip which contains only a thin layer of the analysis fluid. The electrochemical analysis is performed at this point. The preferred method of analysis is amperometry but potentiometry or impedance detection is also used.

8) And the mechanism retracts allowing the cartridge to be removed from the analyzer.

Figure 17:
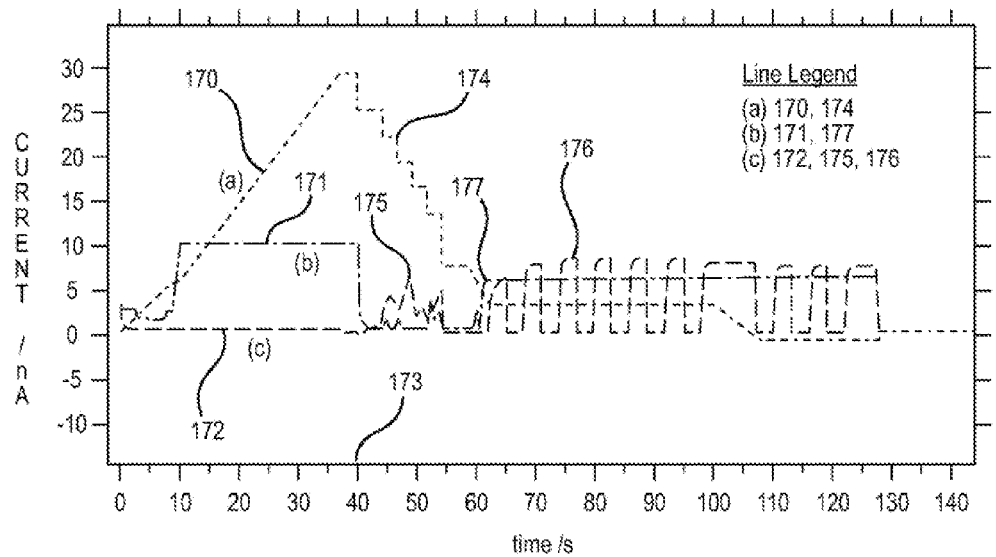
FIG. 17 illustrates the electrochemical response (current versus time), and other responses, of a preferred embodiment of an immunosensor.

Referring now to FIG. 17, there is illustrated an electrical signal 170 representing the position of the electric motor actuating the sample diaphragm 156, the response 171 of the conductimetric electrode, and the electrochemical response 172 of a amperometric immunosensor. In the time period prior to 40 seconds after initiation of the immunoassay 173, the motor depresses the diaphragm, which pushes the sample into the capture region and over the conductimetric sensor. Thus, after about 10 seconds, the conductivity rises to a steady value representative of sample filling the portion of the conduit containing the conductimetric sensor. During this period the valve is sealed by contact with the sample. Between 40 seconds and about 63 seconds, the motor position is stepped back in increments 174, creating a periodic fluctuation in pressure, which draws an air-segmented portion of wash fluid over the sensor. During this period, fluctuations 175 in the immunoassay sensor are seen. At 177, the conductimetric response indicates that the wash fluid, which contains substrate, covers the conductimetric sensor. As the fluid is drawn slowly over the sensor, a potential is applied (in this example, every five seconds, for 2.5 second periods) to the sensor, resulting in response 176, which indicates the presence of analyte bound to the sensor.

The invention described and disclosed herein has numerous benefits and advantages compared to previous devices. These benefits and advantages include, but are not limited to ease of use, the automation of most if not all steps of the analysis, which eliminates user included error in the analysis.

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

What is claimed is:

1. A method of measuring an amount of an analyte using an electrochemical assay in a conduit comprising a sensor, wherein said sensor comprises an electrode having a surface layer of immobilized antibody that binds said analyte, and a counter/reference electrode disposed within said conduit, said method comprising:
    contacting said sensor with a liquid sample containing said analyte;
    contacting said sensor with an enzyme-labeled antibody capable of binding said analyte, whereby a complex of immobilized antibody, analyte and labeled antibody is formed;
    contacting said sensor with a solution comprising a substrate for said enzyme and at least one air segment to remove unbound analyte and labeled antibody from a region of the sensor;
    removing substantially all said solution from said sensor while retaining a portion of said solution over said electrode, said counter/reference electrode, and a contiguous portion of a wall of the conduit connecting said electrodes; and
    detecting a product of a reaction between said enzyme-labeled antibody and said substrate using said sensor, whereby the amount of said analyte in the liquid sample is measured.

2. The method of claim 1, wherein the sample comprises the enzyme-labeled antibody dissolved therein.

3. The method of claim 1, wherein the enzyme-labeled antibody is subsequently delivered in a liquid to the sensor that is not the sample, prior to delivery of said solution.

4. The method of claim 1, wherein the retained portion of said solution comprises a predetermined volume.

5. The method of claim 1, wherein at least a portion of the wall of the conduit is treated to reduce non-specific binding of the enzyme-labeled antibody.

6. The method of claim 1, wherein the at least one air segment is formed by evacuation of the conduit.

7. The method of claim 1, further comprising:
    displacing the liquid sample from the sensor into a waste region prior to the contacting the sensor with the solution; and
    providing the solution in another conduit,
    wherein the contacting the sensor with the solution comprises displacing the solution from the another conduit into contact with the sensor.

8. The method of claim 7, wherein the displacing the liquid sample into the waste region closes a first vent.

9. The method of claim 8, wherein the at least one air segment is formed by forcing air through a second vent into the conduit.

10. The method of claim 9, wherein:
    the displacing the solution further comprises actuating a pump to create a lower pressure in the conduit; and
    the actuating the pump occurs subsequent to the closing the first vent.

11. The method of claim 10, wherein:
    the second vent comprises a membrane that vibrates as the air is forced through the second vent providing an intermittent air stream; and
    the intermittent air stream interrupts displacing the solution from the another conduit into contact with the sensor, and causes the forming the at least one air segment.

* * * * *